United States Patent
Defossa et al.

(10) Patent No.: US 6,812,250 B2
(45) Date of Patent: Nov. 2, 2004

(54) CARBOXAMIDE-SUBSTITUTED PHENYLUREA DERIVATIVES, PROCESS FOR THEIR PREPARATION AND THEIR USE AS MEDICAMENTS

(75) Inventors: Elisabeth Defossa, Idstein (DE); Thomas Klabunde, Frankfurt (DE); Hans-Joerg Burger, Hofheim (DE); Andreas Herling, Bad Camberg (DE); Erich von Roedern, Frankfurt (DE); Stefan Peukert, Frankfurt (DE); Alfons Enhsen, Büttelborn (DE); Armin Bauer, Frankfurt am Main (DE); Bernd Neises, Offenburg (DE); Karl Ulrich Wendt, Frankfurt (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 10/153,597

(22) Filed: May 24, 2002

(65) Prior Publication Data

US 2003/0176497 A1 Sep. 18, 2003

(30) Foreign Application Priority Data

May 25, 2001 (DE) .......................................... 101 25 567
Jan. 21, 2002 (DE) .......................................... 102 07 369

(51) Int. Cl.[7] ..................... C07C 275/16; C07C 275/20; C07C 275/22; A61K 31/17
(52) U.S. Cl. ....................... 514/594; 514/596; 514/597; 564/44; 564/47
(58) Field of Search ..................... 564/44, 47; 514/594, 514/596, 597

(56) References Cited

FOREIGN PATENT DOCUMENTS

| | | |
|---|---|---|
| DE | 29 26 480 | 1/1980 |
| EP | 0 136 745 | 4/1985 |
| EP | 0 167 197 | 1/1986 |
| WO | WO97/26265 | 7/1997 |
| WO | WO97/41097 | 11/1997 |
| WO | WO98/08871 | 3/1998 |
| WO | WO99/03861 | 1/1999 |
| WO | WO00/71506 A2 | 11/2000 |
| WO | WO00/71506 A3 | 11/2000 |
| WO | WO01/94300 A1 | 12/2001 |

OTHER PUBLICATIONS

H. Okada et al., "Synthesis and Antitumor Activities of Prodrugs of Benzoylphenylureas", Chem. Pharm. Bull. vol. 42, No. 1, pp. 57–61 (1994).
P. Drueckes et al., "Photometric Microtiter Assay of Inorganic Phosphate in the Presence of Acid–Labile Organic Phosphates", Analytical Biochemistry, vol. 230, pp. 173–177, (1995).
H.D. Engers et al., "Kinetic Mechanism of Phosphorylase a. I. Initial Velocity Studies", Can. J. Biochem., vol. 48(7), pp. 746–754, (Jan. 12, 1970).
S. Wang et al., "Development of Compound–Specific Elisa for Flufenoxuron and an Improved Class–Specific Assay for Benzoylphenylurea Insect Growth Regulators", J. Agric. Food Chem., vol. 47, pp. 3416–3424, (1999).

*Primary Examiner*—Rita Desai
(74) *Attorney, Agent, or Firm*—Finnegan, Henderson, Farabow, Garrett & Dunner, L.L.P.

(57) ABSTRACT

The invention relates to carboxamide-substituted phenylurea derivatives and their physiologically tolerated salts and physiologically functional derivatives.

Compounds of the formula I

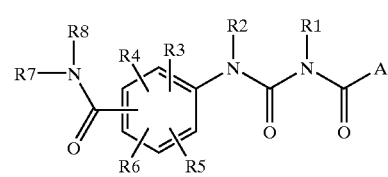

in which the radicals have the stated meanings, and the physiologically tolerated salts thereof and process for their preparation are described. The compounds are suitable, for example, for treating type II diabetes.

6 Claims, No Drawings

CARBOXAMIDE-SUBSTITUTED PHENYLUREA DERIVATIVES, PROCESS FOR THEIR PREPARATION AND THEIR USE AS MEDICAMENTS

This application claims the benefit of foreign priority under 35 U.S.C. §119 of German patent application no. 10125567.5, filed on May 25, 2001 and German patent application no10207369.4, filed on Jan. 21, 2002 the contents of both of which are incorporated by reference herein.

The invention relates to carboxamide-substituted phenylurea derivatives and their physiologically tolerated salts and physiologically functional derivatives.

Acylphenylurea derivatives of similar structure have already been described in the prior art as insecticides (EP 0 136 745, EP 0 167 197, DE 29 26 480, J. Agric. Food Chem. 1999, 47, 3116–3424).

In one embodiment, the invention is based on the object of providing compounds which display a blood glucose-lowering effect which can be utilized in therapy.

The invention therefore, for example, relates to compounds of the formula I,

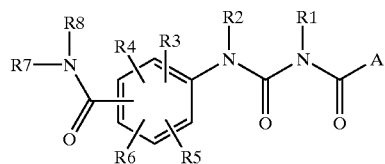

in which

A is phenyl or naphthyl, where the phenyl or naphthyl is unsubstituted or substituted 1, 2, or 3 times wherein each substituent is independently chosen from F, Cl, Br, OH, $CF_3$, $NO_2$, CN, $OCF_3$, O—$(C_1–C_6)$-alkyl, O—$(C_2–C_6)$-alkenyl, O—$(C_2–C_6)$-alkynyl, S—$(C_1–C_6)$-alkyl, S—$(C_2–C_6)$-alkenyl, S—$(C_2–C_6)$-alkynyl, SO—$(C_1–C_6)$-alkyl, $SO_2$—$(C_1–C_6)$-alkyl, $SO_2$—$NH_2$, $(C_1–C_6)$-alkyl, $(C_2–C_6)$-alkenyl, $(C_2–C_6)$-alkynyl, $(C_3–C_7)$-cycloalkyl, $(C_3–C_7)$-cycloalkyl-$(C_1–C_4)$-alkylene, $(C_0–C_6)$-alkylene-COOH, $(C_0–C_6)$-alkylene-COO—$(C_1–C_7)$-alkyl, $(C_0–C_6)$-alkylene-COO—$(C_2–C_7)$-alkenyl, $CONH_2$, CONH—$(C_1–C_6)$-alkyl, CON—$[(C_1–C_6)$-alkyl$]_2$, CONH—$(C_3–C_6)$-cycloalkyl, $(C_0–C_6)$-alkylene-$NH_2$, $(C_0–C_6)$-alkylene-NH—$(C_2–C_6)$-alkyl, $(C_0–C_6)$-alkylene-N—$[(C_1–C_6)$-alkyl$]_2$, NH—CO—$(C_1–C_6)$-alkyl, NH—CO-phenyl, and NH—$SO_2$-phenyl, wherein the phenyl of NH—CO-phenyl and NH—$SO_2$-phenyl is unsubstituted or substituted 1 or 2 times wherein each substituent is independently chosen from F, Cl, CN, OH, $(C_1–C_6)$-alkyl, O—$(C_1–C_6)$-alkyl, $CF_3$, $OCF_3$, COOH, COO—$(C_1–C_6)$-alkyl and $CONH_2$;

R1, R2 are, independently of one another, H, $(C_1–C_6)$-alkyl, O—$(C_1–C_6)$-alkyl, CO—$(C_1–C_6)$-alkyl, or COO—$(C_1–C_6)$-alkyl;

R3, R4, R5, R6 are, independently of one another, H, F, Cl, Br, OH, $CF_3$, $NO_2$, CN, $OCF_3$, O—$(C_1–C_6)$-alkyl, O—$(C_2–C_6)$-alkenyl, O—$(C_2–C_6)$-alkynyl, S—$(C_1–C_6)$-alkyl, S—$(C_2–C_6)$-alkenyl, S—$(C_2–C_6)$-alkynyl, SO—$(C_1–C_6)$-alkyl, $SO_2$—$(C_1–C_6)$-alkyl, $SO_2$—$NH_2$, $(C_1–C_6)$-alkyl, $(C_2–C_6)$-alkenyl, $(C_2–C_6)$-alkynyl, $(C_3–C_7)$-cycloalkyl, $(C_3–C_7)$-cycloalkyl-$(C_1–C_4)$-alkylene, COOH, COO—$(C_1–C_6)$-alkyl, CO—$NH_2$, CO—NH—$(C_1–C_6)$-alkyl, CO—N—$[(C_1–C_6)$-alkyl$]_2$, CO—NH—$(C_3–C_7)$-cycloalkyl, $NH_2$, NH—$(C_1–C_6)$-alkyl, N—$[(C_1–C_6)$-alkyl$]_2$, NH—CO—$(C_1–C_6)$-alkyl, NH—CO-phenyl, or NH—$SO_2$-phenyl, wherein the phenyl of NH—CO-phenyl and NH—$SO_2$-phenyl is unsubstituted or substituted 1 or 2 times wherein each substituent is independently chosen from F, Cl, CN, OH, (C1–C6)-alkyl, O—$(C1–C_6)$-alkyl, $CF_3$, $OCF_3$, COOH, COO—$(C_1–C_6)$-alkyl and CO—$NH_2$;

R7 is H, $(C_1–C_6)$-alkyl, or CO$(C_1–C_6)$-alkyl;

R8 is H, $(C_1–C_{10})$-alkyl, where the alkyl is unsubstituted or substituted 1, 2, or 3 times wherein each substituent is independently chosen from OH, $CF_3$, CN, COOH, COO—$(C_1–C_6)$-alkyl, CO—$NH_2$, $NH_2$, NH—$(C_1–C_6)$-alkyl, N—$[(C_1–C_6)$-alkyl$]_2$, NCO—$(C_1–C_6)$-alkyl, NCOO—$(C_1–C_6)$-alkyl, NCOO—$(C_1–C_6)$-alkenyl, NCOO—$(C_1–C_6)$-alkynyl and NCOO—$(C_1–C_4)$-alkylene-$(C_6–C_{10})$-aryl; or $(CH_2)_m$-aryl, where m ranges from 0–6, and aryl is phenyl, O-phenyl, CO-phenyl, benzo[1,3]dioxolyl, heterocycloalkyl, pyridyl, indolyl, piperidinyl, tetrahydronaphthyl, naphthyl, 2,3-dihydro-benzo[1,4]dioxinyl, benzo[1,2,5]thiadiazolyl, pyrrolidinyl, or morpholinyl, where the aryl is unsubstituted or substituted by at least one R9;

R9 is F, Cl, Br; OH, $NO_2$, $CF_3$, $OCF_3$, $(C_1–C_6)$-alkyl, $(C_1–C_6)$-alkyl-OH, O—$(C_1–C_6)$-alkyl, S—$(C_1–C_6)$-alkyl, $(C_1–C_4)$-alkylphenyl, COOH, or COO—$(C_1–C_6)$-alkyl;

and their physiologically tolerable salts.

In one embodiment, the compounds of the formula I are those in which

A is phenyl, where the phenyl is unsubstituted or substituted 1, 2, or 3 times wherein each substituent is independently chosen from F, Cl, and Br;

R1, R2 are H;

R3, R4, R5, R6 are, independently of one another, H, F, Cl, Br, $NO_2$, O—$(C_1–C_6)$-alkyl, or $(C_1–C_6)$-alkyl;

R7 is H, or $CH_3$;

R8 is H, $(C_1–C_{10})$-alkyl, where the alkyl is unsubstituted or substituted 1, 2, or 3 times wherein each substituent is independently chosen from OH, $CF_3$, CN, COOH, COO—$(C_1–C_6)$-alkyl, CO—$NH_2$, $NH_2$, NH—$(C_1–C_6)$-alkyl, N—$[(C_1–C_6)$-alkyl$]_2$, NCO—$(C_1–C_6)$-alkyl, NCOO—$(C_1–C_6)$-alkyl, NCOO—$(C_1–C_6)$-alkenyl, NCOO—$(C_1–C_6)$-alkynyl or NCOO—$(C_1–C_4)$-alkylene-$(C_6–C_{10})$-aryl; or $(CH2)m$-aryl, where m ranges from 0–6, and aryl is phenyl, O-phenyl, CO-phenyl, benzo[1,3]dioxolyl, heterocycloalkyl, pyridyl, indolyl, piperidinyl, tetrahydronaphthyl, naphthyl, 2,3-dihydro-benzo[1,4]dioxinyl, benzo[1,2,5]thiadiazolyl, pyrrolidinyl, morpholinyl, where the aryl is unsubstituted or substituted by at least one R9;

R9 is F, Cl, Br; OH, $NO_2$, $CF_3$, $OCF_3$, $(C_1–C_6)$-alkyl, $(C_1–C_6)$-alkyl-OH, O—$(C_1–C_6)$-alkyl, S—$(C_1–C_6)$-alkyl, $(C_1–C_4)$-alkylphenyl, COOH, or COO—$(C_1–C_6)$-alkyl;

and their physiologically tolerable salts.

In another embodiment, the compounds of the formula I are those in which

A is phenyl, where the phenyl is unsubstituted or substituted 1, 2, or 3 times wherein each substituent is independently chosen from F, Cl, and Br;

R1, R2 are H;

R3, R4, R5, R6 are, independently of one another, H, F, Cl, Br, NO$_2$, O—(C$_1$–C$_6$)-alkyl, or (C$_1$–C$_6$)-alkyl;

R7 is H, or CH$_3$;

R8 is (C$_1$–C$_{10}$)-alkyl, where the alkyl is unsubstituted or substituted 1, 2, or 3 times wherein each substituent is independently chosen from OH, CF$_3$, CN, COOH, COO—(C$_1$–C$_6$)-alkyl, CO—NH$_2$, NH$_2$, NH—(C$_1$–C$_6$)-alkyl, N—[(C$_1$–C$_6$)-alkyl]$_2$, NCO—(C$_1$–C$_6$)-alkyl, NCOO—(C$_1$–C$_6$)-alkyl, NCOO—(C$_1$–C$_6$)-alkenyl, NCOO—(C$_1$–C$_6$)-alkynyl or NCOO—(C$_1$–C$_4$)-alkylene-(C$_6$–C$_{10}$)-aryl; or (CH$_2$)$_m$-aryl, where m ranges from 0–6, and aryl is phenyl, O-phenyl, CO-phenyl, benzo[1,3]dioxolyl, heterocycloalkyl, pyridyl, indolyl, piperidinyl, tetrahydronaphthyl, naphthyl, 2,3-dihydro-benzo[1,4]dioxinyl, benzo[1,2,5]thiadiazolyl, pyrrolidinyl, morpholinyl, where the aryl is unsubstituted or substituted by at least one R9;

R9 is F, Cl, Br; OH, NO$_2$, CF$_3$, OCF$_3$, (C$_1$–C$_6$)-alkyl, (C$_1$–C$_6$)-alkyl-OH, O—(C$_1$–C$_6$)-alkyl, S—(C$_1$–C$_6$)-alkyl, (C$_1$–C$_4$)-alkylphenyl, COOH, or COO—(C$_1$–C$_6$)-alkyl; and their physiologically tolerable salts.

In one embodiment, the invention further relates to the use of the compounds of the formula I

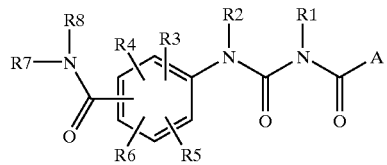

in which

A is phenyl or naphthyl, where the phenyl or naphthyl is unsubstituted or substituted 1, 2, or 3 times wherein each substituent is independently chosen from F, Cl, Br, OH, CF$_3$, NO$_2$, CN, OCF$_3$, O—(C$_1$–C$_6$)-alkyl, O—(C$_2$–C$_6$)-alkenyl, O—(C$_2$–C$_6$)-alkynyl, S—(C$_1$–C$_6$)-alkyl, S—(C$_2$–C$_6$)-alkenyl, S—(C$_2$–C$_6$)-alkynyl, SO—(C$_1$–C$_6$)-alkyl, SO$_2$—(C$_1$–C$_6$)-alkyl, SO$_2$—NH$_2$, (C$_1$–C$_6$)-alkyl, (C$_2$–C$_6$)-alkenyl, (C$_2$–C$_6$)-alkynyl, (C$_3$–C$_7$)-cycloalkyl, (C$_3$–C$_7$)-cycloalkyl-(C$_1$–C$_4$)-alkylene, (C$_0$–C$_6$)-alkylene-COOH, (C$_0$–C$_6$)-alkylene-COO—(C$_1$–C$_7$)-alkyl, (C$_0$–C$_6$)-alkylene-COO—(C$_2$–C$_7$)-alkenyl, CONH$_2$, CONH—(C$_1$–C$_6$)-alkyl, CON—[(C$_1$–C$_6$)-alkyl]$_2$, CONH—(C$_3$–C$_6$)-cycloalkyl, (C$_0$–C$_6$)-alkylene-NH$_2$, (C$_0$–C$_6$)-alkylene-NH—(C$_1$–C$_6$)-alkyl, (C$_0$–C$_6$)-alkylene-N—[(C$_1$–C$_6$)-alkyl]$_2$, NH—CO—(C$_1$–C$_6$)-alkyl, NH—CO-phenyl, NH—SO$_2$-phenyl, wherein the phenyl of NH—CO-phenyl and NH—SO$_2$-phenyl is unsubstituted or substituted 1 or 2 times wherein each substituent is independently chosen from F, Cl, CN, OH, (C$_1$–C$_6$)-alkyl, O—(C$_1$–C$_6$)-alkyl, CF$_3$, OCF$_3$, COOH, COO—(C$_1$–C$_6$)-alkyl and CONH$_2$;

R1, R2 are, independently of one another, H, (C$_1$–C$_6$)-alkyl, O—(C$_1$–C$_6$)-alkyl, CO—(C$_1$–C$_6$)-alkyl, or COO—(C$_1$–C$_6$)-alkyl;

R3, R4, R5, R6 are, independently of one another, H, F, Cl, Br, OH, CF$_3$, NO$_2$, CN, OCF$_3$, O—(C$_1$–C$_6$)-alkyl, O—(C$_2$–C$_6$)-alkenyl, O—(C$_2$–C$_6$)-alkynyl, S—(C$_1$–C$_6$)-alkyl, S—(C$_2$–C$_6$)-alkenyl, S—(C$_2$–C$_6$)-alkynyl, SO—(C$_1$–C$_6$)-alkyl, SO$_2$—(C$_1$–C$_6$)-alkyl, SO$_2$—NH$_2$, (C$_1$–C$_6$)-alkyl, (C$_2$–C$_6$)-alkenyl, (C$_2$–C$_6$)-alkynyl, (C$_3$–C$_7$)-cycloalkyl, (C$_3$–C$_7$)-cycloalkyl-(C$_1$–C$_4$)-alkylene, COOH, COO—(C$_1$–C$_6$)-alkyl, CO—NH$_2$, CO—NH—(C$_1$–C$_6$)-alkyl, CO—N—[(C$_1$–C$_6$)-alkyl]$_2$, CO—NH—(C$_3$–C$_7$)-cycloalkyl, NH$_2$, NH—(C$_1$–C$_6$)-alkyl, N—[(C$_1$–C$_6$)-alkyl]$_2$, NH—CO—(C$_1$–C$_6$)-alkyl, NH—CO-phenyl, or NH—SO$_2$-phenyl, wherein the phenyl of NH—CO-phenyl and NH—SO$_2$-phenyl is unsubstituted or substituted 1 or 2 times wherein each substituent is independently chosen from F, Cl, CN, OH, (C$_1$–C$_6$)-alkyl, O—(C$_1$–C$_6$)-alkyl, CF$_3$, OCF$_3$, COOH, COO—(C$_1$–C$_6$)-alkyl and CO—NH$_2$;

R7 is H, (C$_1$–C$_6$)-alkyl, or CO(C$_1$–C$_6$)-alkyl;

R8 is H, (C$_1$–C$_{10}$)-alkyl, where the alkyl is unsubstituted or substituted 1, 2, or 3 times wherein each substituent is independently chosen from OH, CF$_3$, CN, COOH, COO—(C$_1$–C$_6$)-alkyl, CO—NH$_2$, NH$_2$, NH—(C$_1$–C$_6$)-alkyl, N—[(C$_1$–C$_6$)-alkyl]$_2$, NCO—(C$_1$–C$_6$)-alkyl, NCOO—(C$_1$–C$_6$)-alkyl, NCOO—(C$_1$–C$_6$)-alkenyl, NCOO—(C$_1$–C$_6$)-alkynyl or NCOO—(C$_1$–C$_4$)-alkylene-(C$_6$–C$_{10}$)-aryl; or (CH$_2$)$_m$-aryl, where m can be 0–6, and aryl can be phenyl, O-phenyl, CO-phenyl, benzo[1,3]dioxolyl, heterocycloalkyl, pyridyl, indolyl, piperidinyl, tetrahydronaphthyl, naphthyl, 2,3-dihydro-benzo[1,4]dioxinyl, benzo[1,2,5]thiadiazolyl, pyrrolidinyl, morpholinyl, where the aryl is unsubstituted or substituted by at least one R9;

R9 is F, Cl, Br; OH, NO$_2$, CF$_3$, OCF$_3$, (C$_1$–C$_6$)-alkyl, (C$_1$–C$_6$)-alkyl-OH, O—(C$_1$–C$_6$)-alkyl, S—(C$_1$–C$_6$)-alkyl, (C$_1$–C$_4$)-alkylphenyl, COOH, or COO—(C$_1$–C$_6$)-alkyl;

and their physiologically tolerable salts, for producing a medicament for reducing the blood glucose level and treating type II diabetes. In another embodiments, these compounds are useful in methods for reducing the blood glucose level and treating type II diabetes of a mammal, for example a human.

The compounds of the formula I may be present in the form of their racemates, racemic mixtures, pure enantiomers, and diastereomers, and mixtures thereof. The alkyl radicals in the substituents R1, R2, R3, R4, R5, R6, R7, R8, R9 and A may be both straight-chain and branched.

Pharmaceutically acceptable salts may be particularly suitable for medical applications because of their greater solubility in water compared with the starting or base compounds. In one embodiment, these salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acids, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acids. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion such as, for example, trifluoroacetate likewise belong within the scope of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester which is able, on administration to a mammal such as, for example, to a human, to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57–61. Such prodrugs can be metabolized in vivo to a compound of the invention. These prodrugs may themselves have activity or not.

The compounds of the invention may also exist in various polymorphous forms, for example as amorphous and crystalline polymorphous forms. All polymorphous forms of the compounds of the invention belong within the scope of the invention and are a further aspect of the invention.

All references hereinafter to "compound(s) of formula I" refer to compound(s) of the formula I as described above, and to the salts, solvates and physiologically functional derivatives thereof as described herein.

The compound(s) of the formula (I) may also be administered in combination with other active ingredients.

The amount of a compound of formula I necessary to achieve the desired biological effect depends on a number of factors, for example the specific compound chosen, the intended use, the mode of administration and the clinical condition of the patient. In one embodiment, the daily dose is generally in the range from 0.3 mg to 100 mg (typically from 3 mg to 50 mg) per day and per kilogram of bodyweight, for example 3–10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which may essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of is the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

In one embodiment, suitable pharmaceutical compounds for oral administration may be in the form of separate units such as, for example, capsules, wafers, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet mau be produced by compressing or molding a powder or granules of the compound, where appropriate with one or more additional ingredients. Compressed tablets may be produced by tableting the compound in free-flowing form such as, for example, a powder or granules, where appropriate mixed with a binder, glidant, inert diluent and/or one or more surface-active/dispersing agent(s) in a suitable machine. Molded tablets may be produced by molding the compound which is in powder form and is moistened with an inert liquid diluent in a suitable machine.

In one embodiment, pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

The pharmaceutical compositions suitable for parenteral administration may, for example, comprise sterile aqueous preparations of a compound of formula I, which are isotonic with the blood of the intended recipient. These preparations may be administered intravenously, although administration may also take place by subcutaneous, intramuscular or intradermal injection. These preparations may may be produced by mixing the compound with water and making the resulting solution sterile and isotonic with blood. Injectable compositions of the invention generally contain from 0.1 to 5% by weight of the active compound.

Pharmaceutical compositions suitable for rectal administration may be, for example, in the form of single-dose suppositories. These may be produced by mixing a compound of the formula I with one or more conventional solid carriers, for example cocoa butter, and shaping the resulting mixture.

Pharmaceutical compositions suitable for topical use on the skin are preferably in the form of ointment, crème, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses may be in the form of single plasters which are suitable for long-term close contact with the patient's epidermis. Such plasters, for example, suitably contain the active ingredient in an aqueous solution which is buffered where appropriate, dissolved and/or dispersed in an adhesive or dispersed in a polymer. A suitable active ingredient concentration is, for example, about 1% to 35%, preferably about 3% to 15%. One embodiment, is for the active ingredient to be released by electrotransport or iontophoresis as described, for example, in Pharmaceutical Research, 2(6): 318 (1986).

Further active ingredients suitable for combination products are: all antidiabetics mentioned in chapter 12 of the Rote Liste 2001. They may be combined with the compounds of the formula I of the invention in particular for synergistic improvement of the effect. Administration of the active ingredient combination may take place either by separate administration of the active ingredients to the patients or in the form of combination products in which a plurality of active ingredients are present in one pharmaceutical preparation.

Antidiabetics include insulin and insulin derivatives such as, for example, Lantus® or HMR 1964, GLP-1 derivatives such as, for example, those disclosed in WO 98/08871 of Novo Nordisk A/S, and orally active hypoglycemic active ingredients.

The orally active hypoglycemic active ingredients include, for example, sulfonylureas, biguanide, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside.

In one embodiment of the invention, the compounds of the formula I are administered in combination with a PPAR gamma agonist such as, for example, rosiglitazone, pioglitazone, JTT-501, GI 262570.

In one embodiment of the invention, the compounds of the formula I are administered in combination with PPAR alpha agonist such as, for example, GW 9578, GW 7647.

In one embodiment of the invention, the compounds of the formula I are administered in combination with a mixed PPAR alpha/gamma agonist such as, for example, GW 1536, AVE 8042, AVE 8134, AVE 0847.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, Bay 13-9952, BMS-201038, R-103757.

In one embodiment of the invention, the compounds of the formula I are administered in combination with bile acid adsorption inhibitor such as, for example, HMR 1453.

In one embodiment of the invention, the compounds of the formula I are administered in combination with a CETP inhibitor such as, for example, Bay 194789.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer such as, for example, HMR1171, HMR1586.

In one embodiment of the invention, the compounds of the formula I are administered in combination with an ACAT inhibitor such as, for example, avasimibe.

In one embodiment of the invention, the compounds of the formula I are administered in combination with an antioxidant such as, for example, OPC-14117.

In one embodiment of the invention, the compounds of the formula I are administered in combination with a lipoprotein lipase inhibitor such as, for example, NO-1886.

In one embodiment of the invention, the compounds of the formula I are administered in combination with an ATP citrate lyase inhibitor such as, for example, SB-204990.

In one embodiment of the invention, the compounds of the formula I are administered in combination with a squalene synthetase inhibitor such as, for example, BMS-188494.

In one embodiment of the invention, the compounds of the formula I are administered in combination with a lipoprotein(a) antagonist such as, for example, CI-1027 or nicotinic acid.

In one embodiment of the invention, the compounds of the formula I are administered in combination with a lipase inhibitor such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or gliclazide.

In one embodiment, the compounds of the formula I are administered in combination with a biguanide such as, for example, metformin.

In another embodiment, the compounds of the formula I are administered in combination with a meglitinide such as, for example, repaglinide.

In one embodiment, the compounds of the formula I are administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]-phenyl]methyl]-2,4-thiazolidinedione.

In one embodiment, the compounds of the formula I are administered in combination with an α-glucosidase inhibitor such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipizide, gliclazide or repaglinide.

In one embodiment, the compounds of the formula I are administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART agonists, NPY agonists, MC4 agonists, orexin agonists, H3 agonists, TNF agonists, CRF agonists, CRF BP antagonists, urocortin agonists, β3 agonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormone, growth hormone-releasing compounds, TRH agonists, decoupling protein 2 or 3 modulators, leptin agonists, DA agonists (bromocriptine, Doprexin), lipase/amylase inhibitors, PPAR modulators, RXR modulators or TR-βagonists.

In one embodiment of the invention, the other active ingredient is leptin.

In one embodiment, the other active ingredient is dexamphetamine or amphetamine.

In one embodiment, the other active ingredient is fenfluramine or dexfenfluramine.

In a further embodiment, the other active ingredient is sibutramine.

In one embodiment, the other active ingredient is orlistat.

In one embodiment, the other active ingredient is mazindol or phentermine.

In one embodiment, the compounds of the formula I are administered in combination with dietary fiber materials, preferably insoluble dietary fiber materials such as, for example, Caromax®. Combination with Caromax® is possible in one preparation or by separate administration of compounds of the formula I and Caromax®. Caromax® can moreover be administered in the form of foodstuffs such as, for example, in bakery products or muesli bars.

It is self-evident that any suitable combination of the compounds of the invention with one or more of the aforementioned compounds and optionally one or more other pharmacologically active substances is regarded as falling within the protection conferred by the present invention.

The invention further relates to a process for the preparation of the compounds of the formula I, which comprises obtaining the compounds of the formula I by proceeding in accordance with the following reaction scheme:

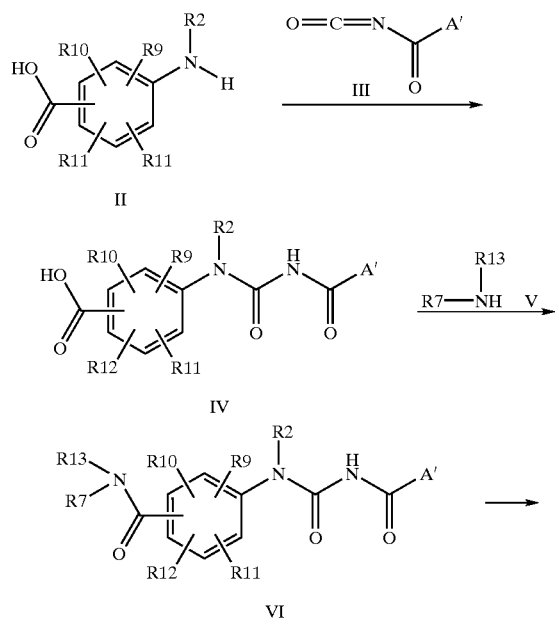

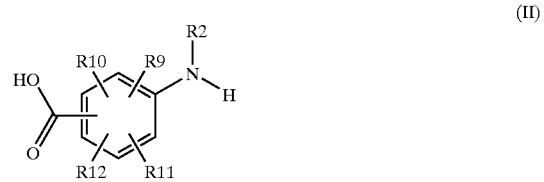

For this purpose, compounds of the formula II $$(II)$$

in which

R9, R10, R11, R 12 are, independently of one another, H, F, Cl, Br, O—(PG-1), CF$_3$, NO$_2$, CN, OCF$_3$, O—(C$_1$–C$_6$)-alkyl, O—(C$_2$–C$_6$)-alkenyl, O—(C$_2$–C$_6$)-alkynyl, S—(C$_1$–C$_6$)-alkyl, S—(C$_2$–C$_6$)-alkenyl, S—(C$_2$–C$_6$)-alkynyl, SO—(C$_1$–C$_6$)-alkyl, SO$_2$—(C$_1$–C$_6$)-alkyl, SO$_2$—N—(PG-2)$_2$, (C$_1$–C$_6$)-alkyl, (C$_2$–C$_6$)-alkenyl, (C$_2$–C$_6$)-alkynyl, (C$_3$–C$_7$)-cycloalkyl, (C$_3$–C$_7$)-cycloalkyl-(C$_1$–C$_4$)-alkylene, COO—(PG-3), COO—(C$_1$–C$_6$)-alkyl, CON—(PG-2)$_2$, CO—NH—(C$_1$–C$_6$)-alkyl, CO—N—[(C$_1$–C$_6$)-alkyl]$_2$, CO—NH—(C$_3$–C$_7$)-cycloalkyl, N—(PG-2)$_2$, NH—(C$_1$–C$_6$)-alkyl, N—[(C$_1$–C$_6$)-alkyl]$_2$, NH—CO—(C$_1$–C$_6$)-alkyl, NH—CO-phenyl, and NH—SO$_2$-phenyl, wherein the phenyl of NH—CO-phenyl and NH—SO$_2$-phenyl is unsubstituted or substituted 1 or 2 times wherein each substituent is independently chosen from F, Cl, CN, O—(PG-1), (C$_1$–C$_6$)-alkyl, O—(C$_1$–C$_6$)-alkyl, CF$_3$, OCF$_3$, COO—(PG-3), COO—(C$_1$–C$_6$)-alkyl and CON—(PG-2)$_2$;

in which R2 has the meaning described above, and

PG-1 is a generally known protective group for alcohols, such as, for example, benzyl, allyl, tetrahydropyranyl or tetrahydrofuranyl;

PG-2 is a generally known protective group for amino groups, such as, for example, (C$_1$–C$_6$)-alkylcarbonyl, (C$_1$–C$_6$)-alkyloxycarbonyl or (C$_6$–C$_{12}$)-aryl-(C$_1$–C$_4$)-alkyloxycarbonyl, which replaces either both hydrogen atoms or only one hydrogen atom in the amino group;

PG-3 is a generally known protective group for esters, such as, for example, (C$_1$–C$_6$)-alkyl, benzyl or p-methoxybenzyl;

are reacted with isocyanates of the formula III $$(III)$$

O=C=N\A'
|
O in which

A' is phenyl or naphthyl, where the phenyl or naphthyl is unsubstituted or substituted 1, 2 or 3 times wherein each substituent is independently chosen from F, Cl, Br, O—PG-1, CF$_3$, NO$_2$, CN, OCF$_3$, O—(C$_1$–C$_6$)-alkyl, O—(C$_2$–C$_6$)-alkenyl, O—(C$_2$–C$_6$)-alkynyl, S—(C$_1$–C$_6$)-alkyl, S—(C$_2$–C$_6$)-alkenyl, S—(C$_2$–C$_6$)- alkynyl, SO—(C$_1$-C$_6$)-alkyl, SO$_2$—(C$_1$-C$_6$)-alkyl, SO$_2$—N-(PG-2)$_2$, (C$_1$-C$_6$)-alkyl, (C$_2$-C$_6$)-alkenyl, (C$_2$-C$_6$)-alkynyl, (C$_3$-C$_7$)-cycloalkyl, (C$_3$-C$_7$)-cycloalkyl-(C$_1$-C$_4$)-alkylene, (C$_0$-C$_6$)-alkylene-COO—(PG-3), (C$_0$-C$_6$)-alkylene-COO—(C$_1$-C$_7$)-alkyl, (C$_0$-C$_6$)-alkylene-COO—(C$_2$-C$_7$)-alkenyl, CO—N—(PG-2)$_2$, CO—NH—(C$_1$-C$_6$)-alkyl, CO—N—[(C$_1$-C$_6$)-alkyl]$_2$, CONH—(C$_3$-C$_6$)-cycloalkyl, (C$_0$-C$_6$)-alkylene-N—(PG-2)$_2$, (C$_0$-C$_6$)-alkylene-NH—(C$_1$-C$_6$)-alkyl, (C$_0$-C$_6$)-alkylene-N—[(C$_1$-C$_6$)-alkyl]$_2$, NH—CO—(C$_1$-C$_6$)-alkyl, NH—CO-phenyl, and NH—SO$_2$-phenyl, wherein the phenyl of NH—CO-phenyl and NH—SO$_2$-phenyl is unsubstituted or substituted 1 or 2 times wherein each substituent is independently chosen from F, Cl, CN, O—(PG-1), (C$_1$-C$_6$)-alkyl, O—(C$_1$-C$_6$)-alkyl, CF$_3$, OCF$_3$, COO—(PG-3), COO—(C$_1$-C$_6$)-alkyl and CO—N-(PG-2)$_2$;

in which PG-3, PG-2 and PG-1 have the meaning described above, in anhydrous organic solvents such as, for example, benzene, toluene or acetonitrile, under a protective gas atmosphere at reaction temperatures between 10° C. and the boiling point of the solvent employed, to give compounds of the formula IV

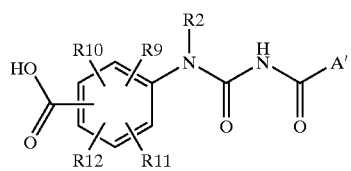
(IV)

in which R2, R9, R10, R11, R12, and A' have the meaning described above.

Compounds of the formula IV are reacted with coupling reagents customary in peptide synthesis, such as, for example, carbodiimides such as dicyclohexylcarbodiimide (DCC) or diisopropylcarbodiimide, carbonyldiazoles such as carbonyldiimidazole and similar reagents, propylphosphonic anhydrides, O-((cyano(ethoxycarbonyl)methylene)amino)-N,N,N',N'-tetramethyluronium tetrafluoroborate (TOTU) and many others, or with formation of the acid chloride, for example using thionyl chloride, with compounds of the formula V

(V)

in which R7 has the meaning described above, and

R13 is (C$_1$-C$_{10}$)-alkyl, where the alkyl is unsubstituted or substituted 1, 2 or 3 time wherein each substituent is independently chosen from O—(PG-1), CF$_3$, CN, COO—(PG-3), COO—(C$_1$-C$_6$)-alkyl, CO—N—(PG-2)$_2$, NH—(PG-2), NH—(C$_1$-C$_6$)-alkyl, N—[(C$_1$-C$_6$)-alkyl]$_2$; phenyl, O-phenyl, CO-phenyl, benzo[1,3]dioxolyl, heterocycloalkyl, pyridyl, indolyl, piperidinyl, tetrahydronaphthyl, naphthyl, 2,3-dihydrobenzo[1,4]dioxinyl, benzo[1,2,5]thiadiazolyl, pyrrolidinyl, and morpholinyl, where the rings are each independently unsubstituted or substituted by at least one R14;

R14 is F, Cl, Br; O—(PG-1), NO$_2$, CF$_3$, OCF$_3$, (C$_1$-C$_6$)-alkyl, (C$_1$-C$_6$)-alkyl-OH, O—(C$_1$-C$_6$)-alkyl, S—(C$_1$-C$_6$)-alkyl, (C$_1$-C$_4$)-alkylphenyl, COO—(PG-3), or COO—(C$_1$-C$_6$)-alkyl;

to give compounds of the formula VI

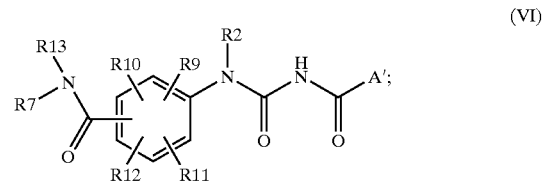
(VI)

the compounds of the formula VI can, if R1 in compounds of the formula I is not a hydrogen atom, be alkylated by reaction with compounds of the formula VII

R15-LG (VII)

in which

LG is a generally known leaving group such as, for example, halogen, arylsulfonyloxy or alkylsulfonyloxy; and R15 is (C$_1$-C$_6$)-alkyl, O—(C$_1$-C$_6$)-alkyl, CO—(C$_1$-C$_6$)-alkyl, or COO—(C$_1$-C$_6$)-alkyl, using a base such as, for example, 1,8-diazabicyclo[5.4.0]undec-7-ene, in organic solvents such as, for example, dichloromethane or acetonitrile, to give compounds of the formula VIII

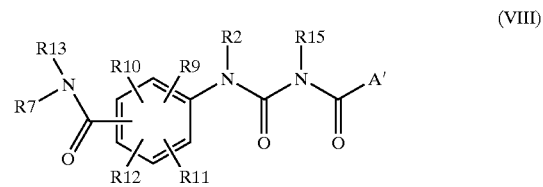
(VIII)

in which R2, R7, R9, R10, R11, R12, R13, R15 and A' have the meaning described above, and after elimination known from the literature of some or all protective groups which may be present, for example, in the radicals R9, R10, R11, R12, R13, R14 and A', compounds of the formula I are obtained. Compounds of the formula I are converted into the salts thereof by adding one equivalent of the appropriate acid or base in an organic solvent such as, for example, acetonitrile or dioxane or in water and by subsequent removal of the solvent.

Another possibility for preparing compounds of the formula I in which R2 is a hydrogen atom is depicted in the following scheme:

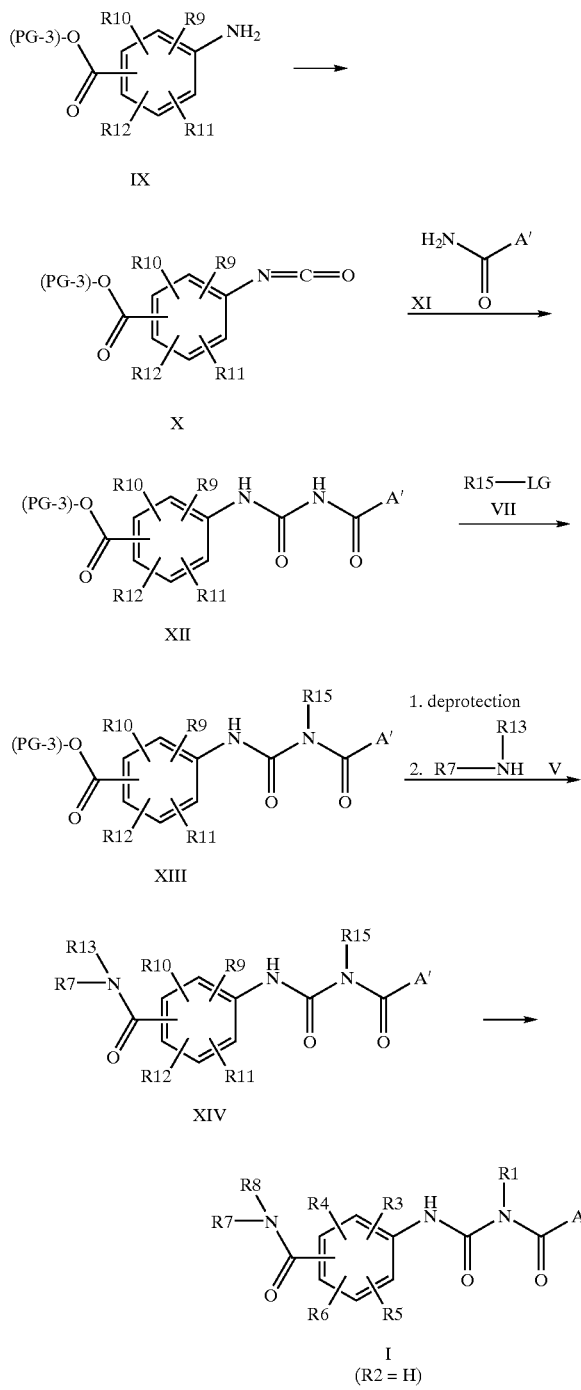

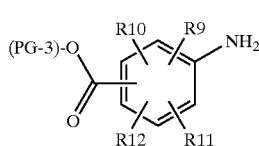

in which compounds of the formula XII in which R9, R10, R11, R12 and PG-3 have the meaning described above, are converted into isocyanates of the formula X

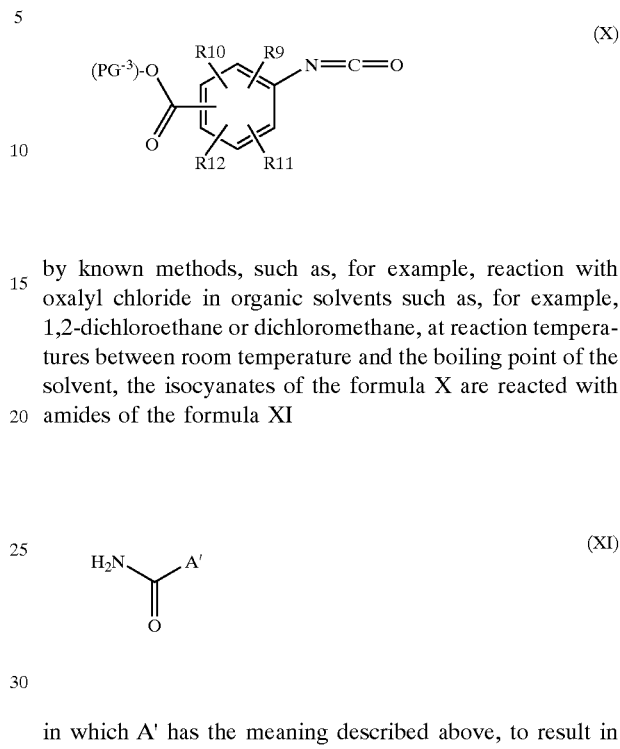

by known methods, such as, for example, reaction with oxalyl chloride in organic solvents such as, for example, 1,2-dichloroethane or dichloromethane, at reaction temperatures between room temperature and the boiling point of the solvent, the isocyanates of the formula X are reacted with amides of the formula XI in which A' has the meaning described above, to result in compounds of the formula XII

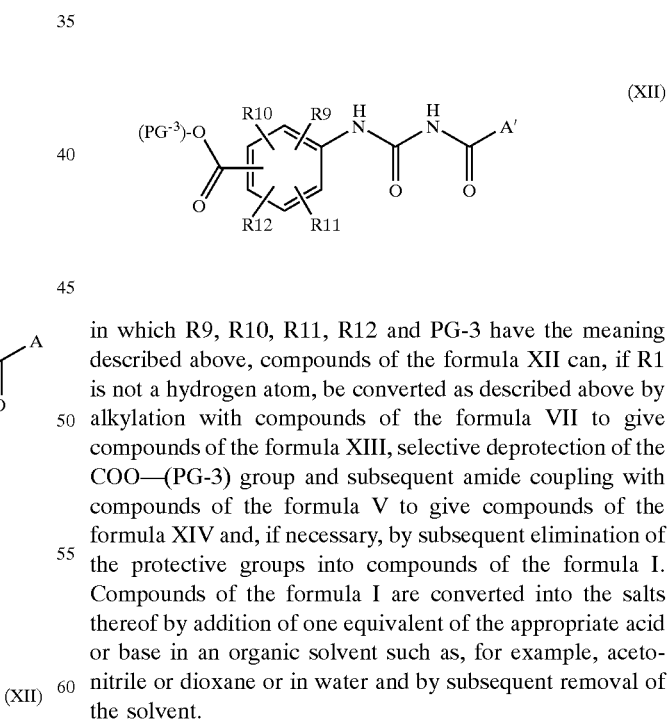

in which R9, R10, R11, R12 and PG-3 have the meaning described above, compounds of the formula XII can, if R1 is not a hydrogen atom, be converted as described above by alkylation with compounds of the formula VII to give compounds of the formula XIII, selective deprotection of the COO—(PG-3) group and subsequent amide coupling with compounds of the formula V to give compounds of the formula XIV and, if necessary, by subsequent elimination of the protective groups into compounds of the formula I. Compounds of the formula I are converted into the salts thereof by addition of one equivalent of the appropriate acid or base in an organic solvent such as, for example, acetonitrile or dioxane or in water and by subsequent removal of the solvent.

The examples detailed below serve to illustrate the invention without, however, restricting it. The measured solidification and decomposition points (Fp.) have not been corrected and generally depend on the heating rate.

TABLE 1

Examples

| Ex. | A | R1* | R2 | R3 | R4 | R6 | R5 | Amide | R7 | R8* | MS**** |
|---|---|---|---|---|---|---|---|---|---|---|---|
| 1 | Phenyl-2-Cl | H | H | 2-Cl | 3-H | 4-H | 6-H | 5 | H | methyl 4-methylpiperidine-1-carboxylate group | ok |
| 2 | Phenyl-2-Cl | H | H | 2-H | 4-H | 5-H | 6-H | 3 | H | methyl 4-methylpiperidine-1-carboxylate group | ok |
| 3 | Phenyl-2-Cl | H | H | 2-H | 4-H | 5-H | 6-H | 3 | H | (CH$_2$)$_5$—OH | ok |
| 4 | Phenyl-2-Cl | H | H | 2-H | 4-H | 5-H | 6-H | 3 | H | (CH$_2$)$_6$—OH | ok |
| 5 | Phenyl-2-Cl | H | H | 2-H | 4-H | 5-H | 6-H | 3 | H | 4-methoxyphenethyl | ok |
| 6 | Phenyl-2-Cl | H | H | 2-H | 4-H | 5-H | 6-H | 3 | H | 3-methoxy-4-hydroxyphenylpropyl | ok |
| 7 | Phenyl-2-Cl | H | H | 2-H | 4-H | 5-H | 6-H | 3 | H | pyrrolidin-1-yl-(CH$_2$)$_4$ | ok |
| 8 | Phenyl-2-Cl | H | H | 2-H | 4-H | 5-H | 6-H | 3 | H | 2-chloro-5-propoxy-nitrophenyl | ok |
| 9 | Phenyl-2-Cl | H | H | 2-H | 4-H | 5-H | 6-H | 3 | H | 4-methoxyphenylpropyl | ok |
| 10 | Phenyl-2-Cl | H | H | 2-H | 4-H | 5-H | 6-H | 3 | H | 4-hydroxyphenylpropyl | ok |
| 11 | Phenyl-2-Cl | H | H | 2-H | 4-H | 5-H | 6-H | 3 | H | 3,4-dihydroxyphenylpropyl | ok |
| 12 | Phenyl-2-Cl | H | H | 2-H | 4-H | 5-H | 6-H | 3 | H | (CH$_2$)$_3$—COOtBu | ok |

TABLE 1-continued

Examples

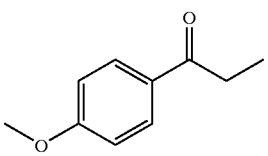

| Ex. | A | R1* | R2 | R3 | R4 | R6 | R5 | Amide | R7 | R8* | MS**** |
|---|---|---|---|---|---|---|---|---|---|---|---|
| 13 | Phenyl-2-Cl | H | H | 2-H | 4-H | 5-H | 6-H | 3 | H | 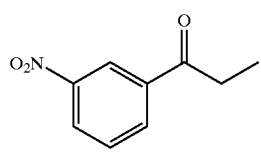 | ok |
| 14 | Phenyl-2-Cl | H | H | 2-H | 4-H | 5-H | 6-H | 3 | H | 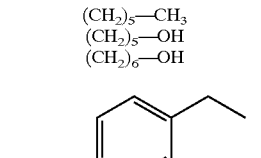 | ok |
| 15 | Phenyl-2-Cl | H | H | 2-H | 4-H | 5-H | 6-H | 3 | H | $(CH_2)_5-CH_3$ | ok |
| 16 | Phenyl-2-Cl | H | H | 2-H | 4-Cl | 5-H | 6-H | 3 | H | $(CH_2)_5-OH$ | ok |
| 17 | Phenyl-2-Cl | H | H | 2-H | 4-Cl | 5-H | 6-H | 3 | H | $(CH_2)_6-OH$ | ok |
| 18 | Phenyl-2-Cl | H | H | 2-H | 4-Cl | 5-H | 6-H | 3 | H | 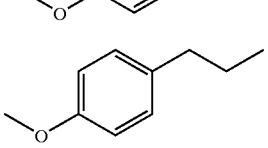 | ok |
| 19 | Phenyl-2-Cl | H | H | 2-H | 4-Cl | 5-H | 6-H | 3 | H | 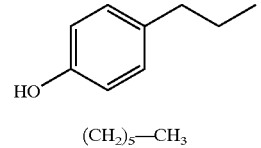 | ok |
| 20 | Phenyl-2-Cl | H | H | 2-H | 4-Cl | 5-H | 6-H | 3 | H | 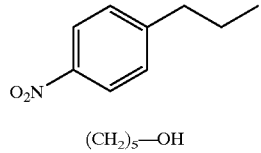 | ok |
| 21 | Phenyl-2-Cl | H | H | 2-H | 4-Cl | 5-H | 6-H | 3 | H | $(CH_2)_5-CH_3$ | ok |
| 22 | Phenyl-2-Cl | H | H | 2-$CH_3$ | 3-H | 4-H | 6-H | 5 | H | 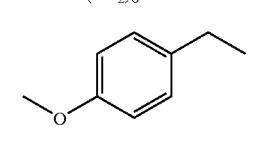 | ok |
| 23 | Phenyl-2-Cl | H | H | 2-$CH_3$ | 3-H | 4-H | 6-H | 5 | H | $(CH_2)_5-OH$ | ok |
| 24 | Phenyl-2-Cl | H | H | 2-$CH_3$ | 3-H | 4-H | 6-H | 5 | H | $(CH_2)_6-OH$ | ok |
| 25 | Phenyl-2-Cl | H | H | 2-$CH_3$ | 3-H | 4-H | 6-H | 5 | H | 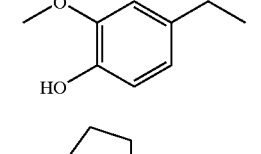 | ok |
| 26 | Phenyl-2-Cl | H | H | 2-$CH_3$ | 3-H | 4-H | 6-H | 5 | H | 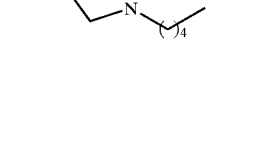 | ok |
| 27 | Phenyl-2-Cl | H | H | 2-$CH_3$ | 3-H | 4-H | 6-H | 5 | H |  | ok |

TABLE 1-continued

Examples

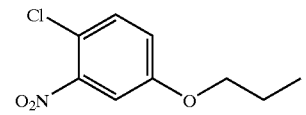

| Ex. | A | R1* | R2 | R3 | R4 | R6 | R5 | Amide | R7 | R8* | MS**** |
|---|---|---|---|---|---|---|---|---|---|---|---|
| 28 | Phenyl-2-Cl | H | H | 2-CH$_3$ | 3-H | 4-H | 6-H | 5 | H | 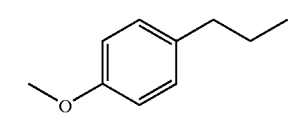 | ok |
| 29 | Phenyl-2-Cl | H | H | 2-CH$_3$ | 3-H | 4-H | 6-H | 5 | H | 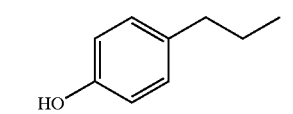 | ok |
| 30 | Phenyl-2-Cl | H | H | 2-CH$_3$ | 3-H | 4-H | 6-H | 5 | H | 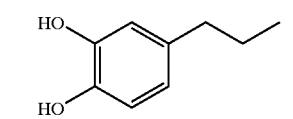 | ok |
| 31 | Phenyl-2-Cl | H | H | 2-CH$_3$ | 3-H | 4-H | 6-H | 5 | H | 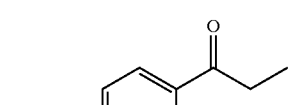 | ok |
| 32 | Phenyl-2-Cl | H | H | 2-CH$_3$ | 3-H | 4-H | 6-H | 5 | H | 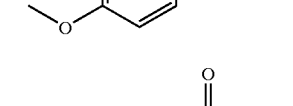 | ok |
| 33 | Phenyl-2-Cl | H | H | 2-CH$_3$ | 3-H | 4-H | 6-H | 5 | H | 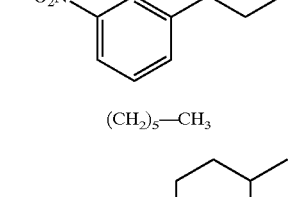 | ok |
| 34 | Phenyl-2-Cl | H | H | 2-CH$_3$ | 3-H | 4-H | 6-H | 5 | H | (CH$_2$)$_5$—CH$_3$ | ok |
| 35 | Phenyl-2-Cl | H | H | 2-OCH$_3$ | 3-H | 4-H | 6-H | 5 | H | 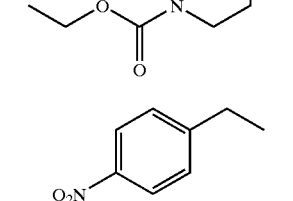 | ok |
| 36 | Phenyl-2-Cl | H | H | 2-OCH$_3$ | 3-H | 4-H | 6-H | 5 | H | 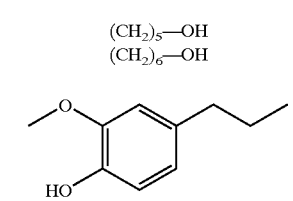 | ok |
| 37 | Phenyl-2-Cl | H | H | 2-OCH$_3$ | 3-H | 4-H | 6-H | 5 | H | (CH$_2$)$_5$—OH | ok |
| 38 | Phenyl-2-Cl | H | H | 2-OCH$_3$ | 3-H | 4-H | 6-H | 5 | H | (CH$_2$)$_6$—OH | ok |
| 39 | Phenyl-2-Cl | H | H | 2-OCH$_3$ | 3-H | 4-H | 6-H | 5 | H |  | ok |

TABLE 1-continued

Examples

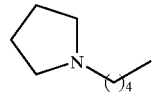

| Ex. | A | R1* | R2 | R3 | R4 | R6 | R5 | Amide | R7 | R8* | MS**** |
|---|---|---|---|---|---|---|---|---|---|---|---|
| 40 | Phenyl-2-Cl | H | H | 2-OCH$_3$ | 3-H | 4-H | 6-H | 5 | H | 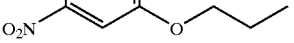 | ok |
| 41 | Phenyl-2-Cl | H | H | 2-OCH$_3$ | 3-H | 4-H | 6-H | 5 | H | 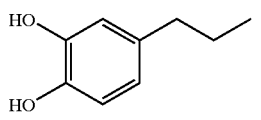 | ok |
| 42 | Phenyl-2-Cl | H | H | 2-OCH$_3$ | 3-H | 4-H | 6-H | 5 | H |  | ok |
| 43 | Phenyl-2-Cl | H | H | 2-OCH$_3$ | 3-H | 4-H | 6-H | 5 | H | (CH$_2$)$_5$—CH$_3$ | ok |
| 44 | Phenyl-2-Cl | H | H | 2-OCH$_3$ | 3-H | 4-H | 6-H | 5 | H | 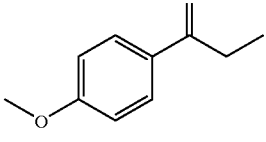 | ok |
| 45 | Phenyl-2-Cl | H | H | 2-OCH$_3$ | 3-H | 4-H | 6-H | 5 | H | 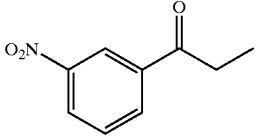 | ok |
| 46 | Phenyl-2-Cl | H | H | 2-OCH$_3$ | 3-H | 4-H | 6-H | 5 | H | 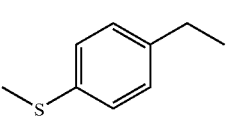 | ok |
| 47 | Phenyl-2-Cl | H | H | 2-H | 4-NO$_2$ | 5-H | 6-H | 3 | H | 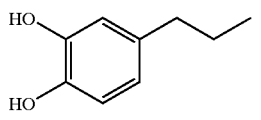 | ok |
| 48 | Phenyl-2-Cl | H | H | 2-H | 4-NO$_2$ | 5-H | 6-H | 3 | H | (CH$_2$)$_5$—OH | ok |
| 49 | Phenyl-2-Cl | H | H | 2-H | 4-NO$_2$ | 5-H | 6-H | 3 | H | (CH$_2$)$_6$—OH | ok |
| 50 | Phenyl-2-Cl | H | H | 2-H | 4-NO$_2$ | 5-H | 6-H | 3 | H | (CH$_2$)$_5$—CH$_3$ | ok |
| 51 | Phenyl-2-Cl | H | H | 2-H | 4-H | 5-H | 6-H | 3 | H | (CH$_2$)$_3$—COOH | ok |
| 52 | Phenyl-2-Cl | H | H | 2-OCH$_3$ | 3-H | 4-H | 6-H | 5 | H | (CH$_2$)$_3$—COOH | ok |
| 53 | Phenyl-2,6-Cl$_2$ | H | H | 2-OCH$_3$ | 3-H | 4-H | 6-H | 5 | H | 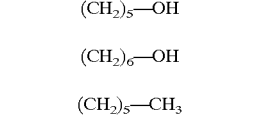 | ok |

TABLE 1-continued
Examples
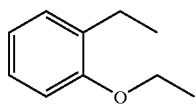
| Ex. | A | R1* | R2 | R3 | R4 | R6 | R5 | Amide | R7 | R8* | MS**** |
|---|---|---|---|---|---|---|---|---|---|---|---|
| 54 | Phenyl-2,6-Cl$_2$ | H | H | 2-OCH$_3$ | 3-H | 4-H | 6-H | 5 | H | 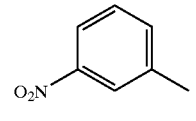 | ok |
| 55 | Phenyl-2,6-Cl$_2$ | H | H | 2-OCH$_3$ | 3-H | 4-H | 6-H | 5 | H | 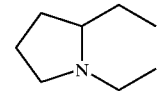 | ok |
| 56 | Phenyl-2-Cl | H | H | 2-OCH$_3$ | 3-H | 4-H | 6-H | 5 | H | 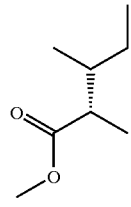 | ok |
| 57 | Phenyl-2-Cl | H | H | 2-OCH$_3$ | 3-H | 4-H | 6-H | 5 | H | 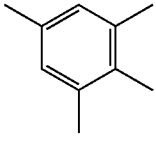 | ok |
| 58 | Phenyl-2-Cl | H | H | 2-OCH$_3$ | 3-H | 4-H | 6-H | 5 | H | 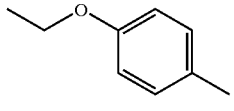 | ok |
| 59 | Phenyl-2-Cl | H | H | 2-OCH$_3$ | 3-H | 4-H | 6-H | 5 | H | 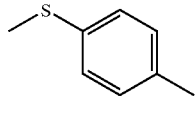 | ok |
| 60 | Phenyl-2-Cl | H | H | 2-OCH$_3$ | 3-H | 4-H | 6-H | 5 | H | 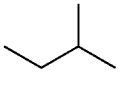 | ok |
| 61 | Phenyl-2-Cl | H | H | 2-OCH$_3$ | 3-H | 4-H | 6-H | 5 | H | 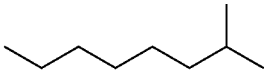 | ok |
| 62 | Phenyl-2-Cl | H | H | 2-OCH$_3$ | 3-H | 4-H | 6-H | 5 | H | 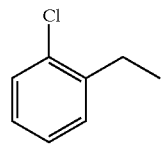 | ok |
| 63 | Phenyl-2-Cl | H | H | 2-OCH$_3$ | 3-H | 4-H | 6-H | 5 | H |  | ok |

TABLE 1-continued
Examples
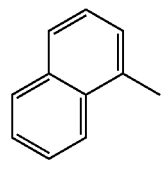
| Ex. | A | R1* | R2 | R3 | R4 | R6 | R5 | Amide | R7 | R8* | MS**** |
|---|---|---|---|---|---|---|---|---|---|---|---|
| 64 | Phenyl-2-Cl | H | H | 2-OCH$_3$ | 3-H | 4-H | 6-H | 5 | H | 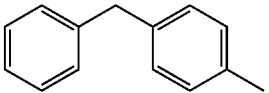 | ok |
| 65 | Phenyl-2-Cl | H | H | 2-OCH$_3$ | 3-H | 4-H | 6-H | 5 | H | 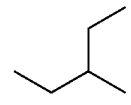 | ok |
| 66 | Phenyl-2-Cl | H | H | 2-OCH$_3$ | 3-H | 4-H | 6-H | 5 | H | 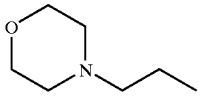 | ok |
| 67 | Phenyl-2-Cl | H | H | 2-OCH$_3$ | 3-H | 4-H | 6-H | 5 | H | 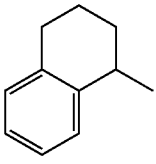 | ok |
| 68 | Phenyl-2-Cl | H | H | 2-OCH$_3$ | 3-H | 4-H | 6-H | 5 | H | 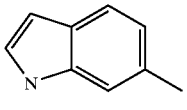 | ok |
| 69 | Phenyl-2-Cl | H | H | 2-OCH$_3$ | 3-H | 4-H | 6-H | 5 | H | 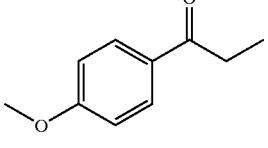 | ok |
| 70 | Phenyl-2-Cl | H | H | 2-H | 4-NO$_2$ | 5-H | 6-H | 3 | H | 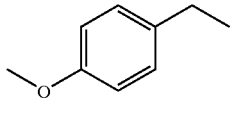 | ok |
| 71 | Phenyl-2-Cl | H | H | 2-H | 4-NO$_2$ | 5-H | 6-H | 3 | H | 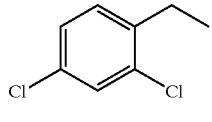 | ok |
| 72 | Phenyl-2-Cl | H | H | 2-OCH$_3$ | 3-H | 4-H | 6-H | 5 | H | 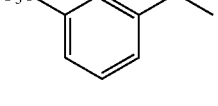 | ok |
| 73 | Phenyl-2-Cl | H | H | 2-OCH$_3$ | 3-H | 4-H | 6-H | 5 | H |  | ok |
| 74 | Phenyl-2-Cl | H | H | 2-OCH$_3$ | 3-H | 4-H | 6-H | 5 | H | CH$_2$—CF$_3$ | ok |

TABLE 1-continued
Examples
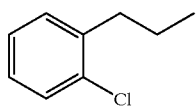
| Ex. | A | R1* | R2 | R3 | R4 | R6 | R5 | Amide | R7 | R8* | MS**** |
|---|---|---|---|---|---|---|---|---|---|---|---|
| 75 | Phenyl-2-Cl | H | H | 2-OCH₃ | 3-H | 4-H | 6-H | 5 | H | 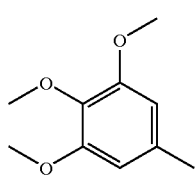 | ok |
| 76 | Phenyl-2-Cl | H | H | 2-OCH₃ | 3-H | 4-H | 6-H | 5 | H | 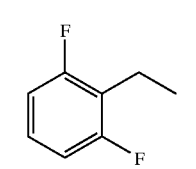 | ok |
| 77 | Phenyl-2-Cl | H | H | 2-OCH₃ | 3-H | 4-H | 6-H | 5 | H | 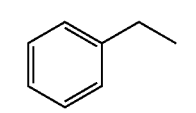 | ok |
| 78 | Phenyl-2-Cl | H | H | 2-OCH₃ | 3-H | 4-H | 6-H | 5 | H | 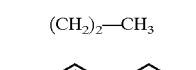 | ok |
| 79 | Phenyl-2-Cl | H | H | 2-OCH₃ | 3-H | 4-H | 6-H | 5 | H | (CH₂)₂—CH₃ | ok |
| 80 | Phenyl-2-Cl | H | H | 2-OCH₃ | 3-H | 4-H | 6-H | 5 | H | 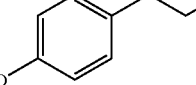 | ok |
| 81 | Phenyl-2-Cl | H | H | 2-OCH₃ | 3-H | 4-H | 6-H | 5 | H | 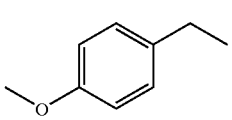 | ok |
| 82 | Phenyl-2-Cl | H | H | 2-OCH₃ | 3-H | 4-H | 6-H | 5 | H | 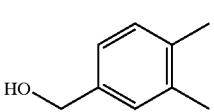 | ok |
| 83 | Phenyl-2-Cl | H | H | 2-OCH₃ | 3-H | 4-H | 6-H | 5 | H | 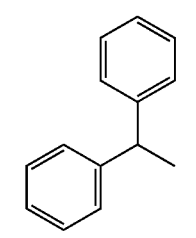 | ok |
| 84 | Phenyl-2-Cl | H | H | 2-OCH₃ | 3-H | 4-H | 6-H | 5 | H | 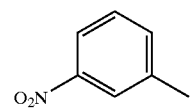 | ok |

TABLE 1-continued
Examples
| Ex. | A | R1* | R2 | R3 | R4 | R6 | R5 | Amide | R7 | R8* | MS**** |
|---|---|---|---|---|---|---|---|---|---|---|---|
| 85 | Phenyl-2-Cl | H | H | 2-OCH₃ | 3-H | 4-H | 6-H | 5 | H | 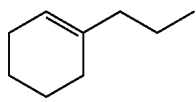 | ok |
| 86 | Phenyl-2-Cl | H | H | 2-OCH₃ | 3-H | 4-H | 6-H | 5 | H |  | ok |
| 87 | Phenyl-2-Cl | H | H | 2-OCH₃ | 3-H | 4-H | 6-H | 5 | H | 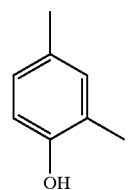 | ok |
| 88 | Phenyl-2-Cl | H | H | 2-OCH₃ | 3-H | 4-H | 6-H | 5 | H | 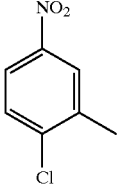 | ok |
| 89 | Phenyl-2-Cl | H | H | 2-OCH₃ | 3-H | 4-H | 6-H | 5 | H | 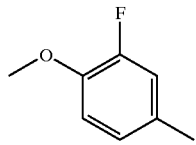 | ok |
| 90 | Phenyl-2-Cl | H | H | 2-OCH₃ | 3-H | 4-H | 6-H | 5 | H | 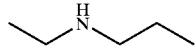 | ok |
| 91 | Phenyl-2-Cl | H | H | 2-OCH₃ | 3-H | 4-H | 6-H | 5 | H | 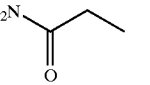 | ok |
| 92 | Phenyl-2-Cl | H | H | 2-OCH₃ | 3-H | 4-H | 6-H | 5 | H | 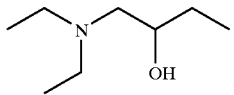 | ok |
| 93 | Phenyl-2-Cl | H | H | 2-OCH₃ | 3-H | 4-H | 6-H | 5 | H | 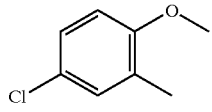 | ok |

TABLE 1-continued

Examples

| Ex. | A | R1* | R2 | R3 | R4 | R6 | R5 | Amide | R7 | R8* | MS**** |
|---|---|---|---|---|---|---|---|---|---|---|---|
| 94 | Phenyl-2,4-Cl$_2$ | Na | H | 2-OCH$_3$ | 3-H | 4-H | 6-H | 5 | H | 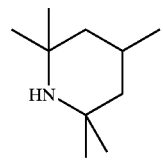 | ok |
| 95 | Phenyl-2,4-Cl$_2$ | Na | H | 2-OCH$_3$ | 3-H | 4-H | 6-H | 5 | H | 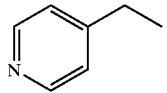 | ok |
| 96 | Phenyl-2,4-Cl$_2$ | Na | H | 2-OCH$_3$ | 3-H | 4-H | 6-H | 5 | H | 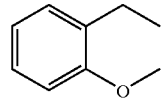 | ok |
| 97 | Phenyl-2,4-Cl$_2$ | Na | H | 2-OCH$_3$ | 3-H | 4-H | 6-H | 5 | H | 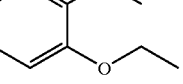 | ok |
| 98 | Phenyl-2,4-Cl$_2$ | Na | H | 2-OCH$_3$ | 3-H | 4-H | 6-H | 5 | H | 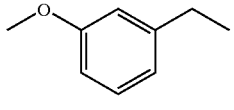 | ok |
| 99 | Phenyl-2,4-Cl$_2$ | Na | H | 2-OCH$_3$ | 3-H | 4-H | 6-H | 5 | H | 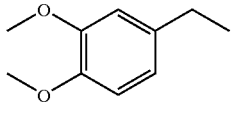 | ok |
| 100 | Phenyl-2,4-Cl$_2$ | Na | H | 2-OCH$_3$ | 3-H | 4-H | 6-H | 5 | H | 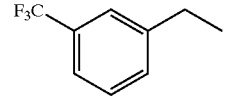 | ok |
| 101 | Phenyl-2,4-Cl$_2$ | Na | H | 2-OCH$_3$ | 3-H | 4-H | 6-H | 5 | H | 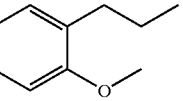 | ok |
| 102 | Phenyl-2,4-Cl$_2$ | Na | H | 2-OCH$_3$ | 3-H | 4-H | 6-H | 5 | H | 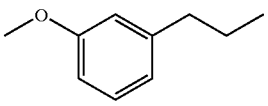 | ok |
| 103 | Phenyl-2,4-Cl$_2$ | Na | H | 2-OCH$_3$ | 3-H | 4-H | 6-H | 5 | H | 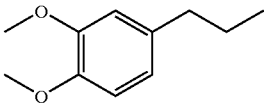 | ok |
| 104 | Phenyl-2,4-Cl$_2$ | Na | H | 2-OCH$_3$ | 3-H | 4-H | 6-H | 5 | H | 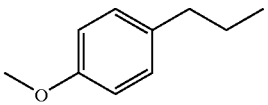 | ok |

TABLE 1-continued
Examples
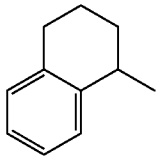
| Ex. | A | R1* | R2 | R3 | R4 | R6 | R5 | Amide | R7 | R8* | MS**** |
|---|---|---|---|---|---|---|---|---|---|---|---|
| 105 | Phenyl-2,4-Cl$_2$ | Na | H | 2-OCH$_3$ | 3-H | 4-H | 6-H | 5 | H | (CH$_2$)$_5$—CN | ok |
| 106 | Phenyl-2,4-Cl$_2$ | Na | H | 2-OCH$_3$ | 3-H | 4-H | 6-H | 5 | H | 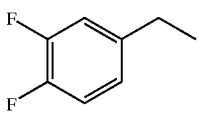 | ok |
| 107 | Phenyl-2,4-Cl$_2$ | Na | H | 2-OCH$_3$ | 3-H | 4-H | 6-H | 5 | H | 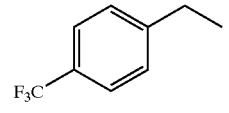 | ok |
| 108 | Phenyl-2,4-Cl$_2$ | Na | H | 2-OCH$_3$ | 3-H | 4-H | 6-H | 5 | H | 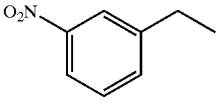 | ok |
| 109 | Phenyl-2,4-Cl$_2$ | Na | H | 2-OCH$_3$ | 3-H | 4-H | 6-H | 5 | H | 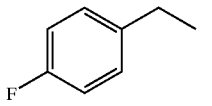 | ok |
| 110 | Phenyl-2,4-Cl$_2$ | Na | H | 2-OCH$_3$ | 3-H | 4-H | 6-H | 5 | H | 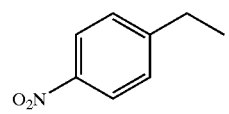 | ok |
| 111 | Phenyl-2,4-Cl$_2$ | Na | H | 2-OCH$_3$ | 3-H | 4-H | 6-H | 5 | H | 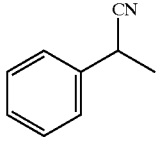 | ok |
| 112 | Phenyl-2,4-Cl$_2$ | Na | H | 2-OCH$_3$ | 3-H | 4-H | 6-H | 5 | H | 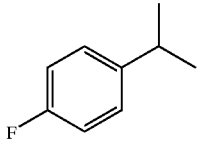 | ok |
| 113 | Phenyl-2,4-Cl$_2$ | Na | H | 2-OCH$_3$ | 3-H | 4-H | 6-H | 5 | H | 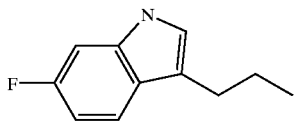 | ok |
| 114 | Phenyl-2,4-Cl$_2$ | Na | H | 2-OCH$_3$ | 3-H | 4-H | 6-H | 5 | H |  | ok |

TABLE 1-continued
Examples
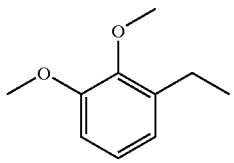
| Ex. | A | R1* | R2 | R3 | R4 | R6 | R5 | Amide | R7 | R8* | MS**** |
|---|---|---|---|---|---|---|---|---|---|---|---|
| 115 | Phenyl-2,4-Cl$_2$ | Na | H | 2-OCH$_3$ | 3-H | 4-H | 6-H | 5 | H | 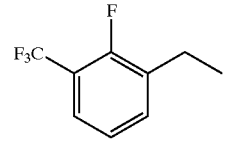 | ok |
| 116 | Phenyl-2,4-Cl$_2$ | Na | H | 2-OCH$_3$ | 3-H | 4-H | 6-H | 5 | H | 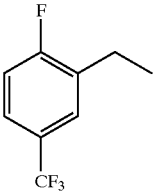 | ok |
| 117 | Phenyl-2,4-Cl$_2$ | Na | H | 2-OCH$_3$ | 3-H | 4-H | 6-H | 5 | H | 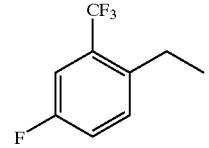 | ok |
| 118 | Phenyl-2,4-Cl$_2$ | Na | H | 2-OCH$_3$ | 3-H | 4-H | 6-H | 5 | H | 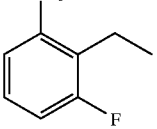 | ok |
| 119 | Phenyl-2,4-Cl$_2$ | Na | H | 2-OCH$_3$ | 3-H | 4-H | 6-H | 5 | H | 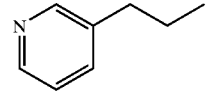 | ok |
| 120 | Phenyl-2,4-Cl$_2$ | Na | H | 2-OCH$_3$ | 3-H | 4-H | 6-H | 5 | H | 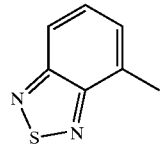 | ok |
| 121 | Phenyl-2,4-Cl$_2$ | Na | H | 2-OCH$_3$ | 3-H | 4-H | 6-H | 5 | H | 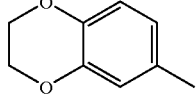 | ok |
| 122 | Phenyl-2,4-Cl$_2$ | Na | H | 2-OCH$_3$ | 3-H | 4-H | 6-H | 5 | H | 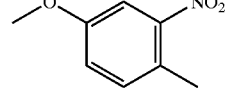 | ok |
| 123 | Phenyl-2,4-Cl$_2$ | Na | H | 2-OCH$_3$ | 3-H | 4-H | 6-H | 5 | H |  | ok |

TABLE 1-continued
Examples
| Ex. | A | R1* | R2 | R3 | R4 | R6 | R5 | Amide | R7 | R8* | MS**** |
|---|---|---|---|---|---|---|---|---|---|---|---|
| 124 | Phenyl-2,4-Cl$_2$ | Na | H | 2-OCH$_3$ | 3-H | 4-H | 6-H | 5 | H | 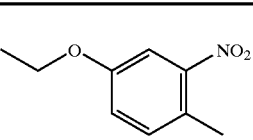 | ok |
| 125 | Phenyl-2,4-Cl$_2$ | Na | H | 2-OCH$_3$ | 3-H | 4-H | 6-H | 5 | H | 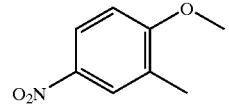 | ok |
| 126 | Phenyl-2,4-Cl$_2$ | Na | H | 2-OCH$_3$ | 3-H | 4-H | 6-H | 5 | H | 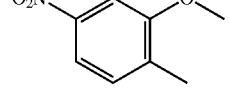 | ok |
| 127 | Phenyl-2,4-Cl$_2$ | Na | H | 2-OCH$_3$ | 3-H | 4-H | 6-H | 5 | H | 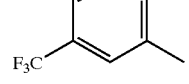 | ok |
| 128 | Phenyl-2,4-Cl$_2$ | Na | H | 2-OCH$_3$ | 3-H | 4-H | 6-H | 5 | H | 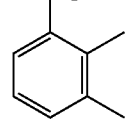 | ok |
| 129 | Phenyl-2,4-Cl$_2$ | Na | H | 2-OCH$_3$ | 3-H | 4-H | 6-H | 5 | H | 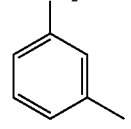 | ok |
| 130 | Phenyl-2,4-Cl$_2$ | Na | H | 2-OCH$_3$ | 3-H | 4-H | 6-H | 5 | H | 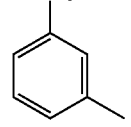 | ok |
| 131 | Phenyl-2,4-Cl$_2$ | Na | H | 2-OCH$_3$ | 3-H | 4-H | 6-H | 5 | H | 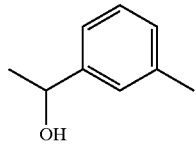 | ok |
| 132 | Phenyl-2,4-Cl$_2$ | Na | H | 2-OCH$_3$ | 3-H | 4-H | 6-H | 5 | H | 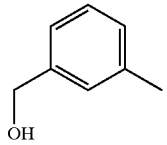 | ok |

TABLE 1-continued
Examples
| Ex. | A | R1* | R2 | R3 | R4 | R6 | R5 | Amide | R7 | R8* | MS**** |
|---|---|---|---|---|---|---|---|---|---|---|---|
| 133 | Phenyl-2,4-Cl$_2$ | Na | H | 2-OCH$_3$ | 3-H | 4-H | 6-H | 5 | H | 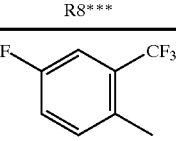 | ok |
| 134 | Phenyl-2,4-Cl$_2$ | Na | H | 2-OCH$_3$ | 3-H | 4-H | 6-H | 5 | H | 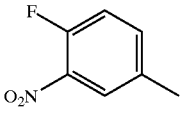 | ok |
| 135 | Phenyl-2,4-Cl$_2$ | Na | H | 2-OCH$_3$ | 3-H | 4-H | 6-H | 5 | H | 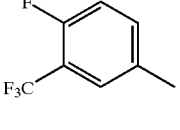 | ok |
| 136 | Phenyl-2,4-Cl$_2$ | Na | H | 2-OCH$_3$ | 3-H | 4-H | 6-H | 5 | H | 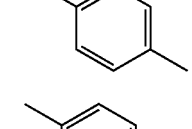 | ok |
| 137 | Phenyl-2,4-Cl$_2$ | Na | H | 2-OCH$_3$ | 3-H | 4-H | 6-H | 5 | H | 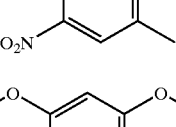 | ok |
| 138 | Phenyl-2,4-Cl$_2$ | Na | H | 2-OCH$_3$ | 3-H | 4-H | 6-H | 5 | H | 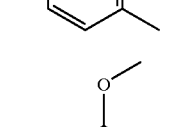 | ok |
| 139 | Phenyl-2,4-Cl$_2$ | Na | H | 2-OCH$_3$ | 3-H | 4-H | 6-H | 5 | H | 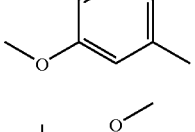 | ok |
| 140 | Phenyl-2,4-Cl$_2$ | Na | H | 2-OCH$_3$ | 3-H | 4-H | 6-H | 5 | H | 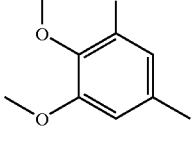 | ok |
| 141 | Phenyl-2,4-Cl$_2$ | Na | H | 2-OCH$_3$ | 3-H | 4-H | 6-H | 5 | H | 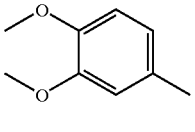 | ok |
| 142 | Phenyl-2,4-Cl$_2$ | Na | H | 2-OCH$_3$ | 3-H | 4-H | 6-H | 5 | H | 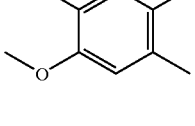 | ok |

TABLE 1-continued
Examples
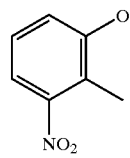
| Ex. | A | R1* | R2 | R3 | R4 | R6 | R5 | Amide | R7 | R8* | MS**** |
|---|---|---|---|---|---|---|---|---|---|---|---|
| 143 | Phenyl-2,4-Cl$_2$ | Na | H | 2-OCH$_3$ | 3-H | 4-H | 6-H | 5 | H | 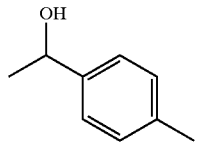 | ok |
| 144 | Phenyl-2,4-Cl$_2$ | Na | H | 2-OCH$_3$ | 3-H | 4-H | 6-H | 5 | H | 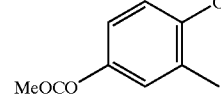 | ok |
| 145 | Phenyl-2,4-Cl$_2$ | Na | H | 2-OCH$_3$ | 3-H | 4-H | 6-H | 5 | H | 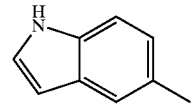 | ok |
| 146 | Phenyl-2,4-Cl$_2$ | Na | H | 2-OCH$_3$ | 3-H | 4-H | 6-H | 5 | H | 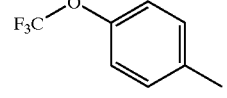 | ok |
| 147 | Phenyl-2,4-Cl$_2$ | Na | H | 2-OCH$_3$ | 3-H | 4-H | 6-H | 5 | H | 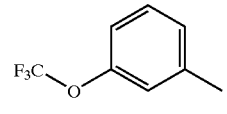 | ok |
| 148 | Phenyl-2,4-Cl$_2$ | Na | H | 2-OCH$_3$ | 3-H | 4-H | 6-H | 5 | H | 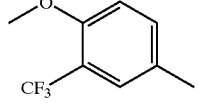 | ok |
| 149 | Phenyl-2,4-Cl$_2$ | Na | H | 2-OCH$_3$ | 3-H | 4-H | 6-H | 5 | H | 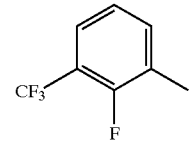 | ok |
| 150 | Phenyl-2,4-Cl$_2$ | Na | H | 2-OCH$_3$ | 3-H | 4-H | 6-H | 5 | H | 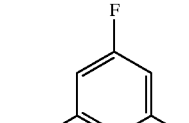 | ok |
| 151 | Phenyl-2,4-Cl$_2$ | Na | H | 2-OCH$_3$ | 3-H | 4-H | 6-H | 5 | H | 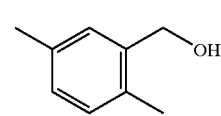 | ok |
| 152 | Phenyl-2,4-Cl$_2$ | Na | H | 2-OCH$_3$ | 3-H | 4-H | 6-H | 5 | H | | ok |

TABLE 1-continued

Examples

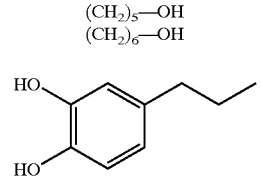

| Ex. | A | R1* | R2 | R3 | R4 | R6 | R5 | Amide | R7 | R8* | MS**** |
|---|---|---|---|---|---|---|---|---|---|---|---|
| 153 | Phenyl-2-Cl | H | H | 2-H | 4-H | 5-NO$_2$ | 6-H | 3 | H | (CH$_2$)$_5$—OH | ok |
| 154 | Phenyl-2-Cl | H | H | 2-H | 4-H | 5-NO$_2$ | 6-H | 3 | H | (CH$_2$)$_6$—OH | ok |
| 155 | Phenyl-2-Cl | H | H | 2-H | 4-H | 5-NO$_2$ | 6-H | 3 | H | 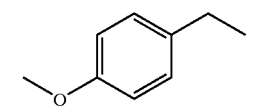 | ok |
| 156 | Phenyl-2-Cl | H | H | 2-H | 4-H | 5-NO$_2$ | 6-H | 3 | H | 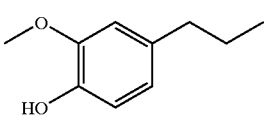 | ok |
| 157 | Phenyl-2-Cl | H | H | 2-F | 4-F | 5-F | 6-H | 3 | H | 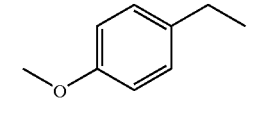 | ok |
| 158 | Phenyl-2-Cl | H | H | 2-F | 4-F | 5-F | 6-H | 3 | H | 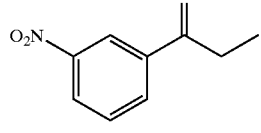 | ok |
| 159 | Phenyl-2-Cl | H | H | 2-F | 4-F | 5-F | 6-H | 3 | H | 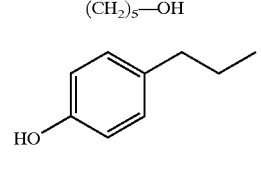 | ok |
| 160 | Phenyl-2-Cl | H | H | 2-F | 3-H | 4-H | 6-H | 5 | H | (CH$_2$)$_5$—OH | ok |
| 161 | Phenyl-2-Cl | H | H | 2-F | 3-H | 4-H | 6-H | 5 | H | 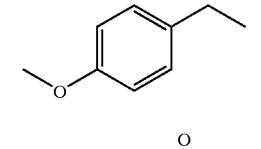 | ok |
| 162 | Phenyl-2-Cl | H | H | 2-F | 3-H | 4-H | 6-H | 5 | H | 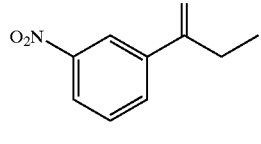 | ok |
| 163 | Phenyl-2-Cl | H | H | 2-F | 3-H | 4-H | 6-H | 5 | H | | ok |
| 164 | Phenyl-2,4-Cl$_2$ | H | H | 2-H | 4-H | 5-NO$_2$ | 6-H | 3 | H | (CH$_2$)$_5$—OH | ok |
| 165 | Phenyl-2,4-Cl$_2$ | H | H | 2-F | 4-F | 5-F | 6-H | 3 | H | (CH$_2$)$_5$—OH | ok |
| 166 | Phenyl-2,4-Cl$_2$ | H | H | 2-F | 4-F | 5-F | 6-H | 3 | H | (CH$_2$)$_6$—OH | ok |
| 167 | Phenyl-2,4-Cl$_2$ | H | H | 2-F | 3-H | 4-H | 6-H | 5 | H | (CH$_2$)$_5$—OH | ok |
| 168 | Phenyl-2,4-Cl$_2$ | H | H | 2-F | 3-H | 4-H | 6-H | 5 | H | (CH$_2$)$_6$—OH | ok |

TABLE 1-continued
Examples
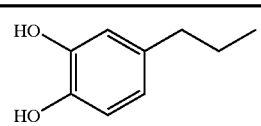
| Ex. | A | R1* | R2 | R3 | R4 | R6 | R5 | Amide | R7 | R8* | MS**** |
|---|---|---|---|---|---|---|---|---|---|---|---|
| 169 | Phenyl-2,4-Cl$_2$ | H | H | 2-F | 3-H | 4-H | 6-H | 5 | H | 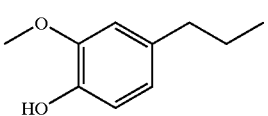 | ok |
| 170 | Phenyl-2,4-Cl$_2$ | H | H | 2-F | 3-H | 4-H | 6-H | 5 | H | 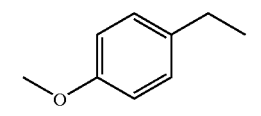 | ok |
| 171 | Phenyl-2,4-Cl$_2$ | H | H | 2-F | 3-H | 4-H | 6-H | 5 | H | 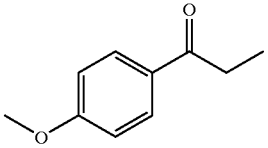 | ok |
| 172 | Phenyl-2,4-Cl$_2$ | H | H | 2-F | 3-H | 4-H | 6-H | 5 | H | 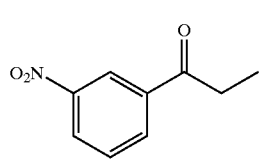 | ok |
| 173 | Phenyl-2,4-Cl$_2$ | H | H | 2-F | 3-H | 4-H | 6-H | 5 | H | 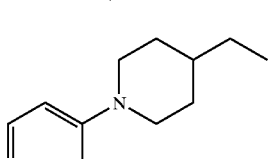 | ok |
| 174 | Phenyl-2,4-Cl$_2$ | H | H | 2-OCH$_3$ | 3-H | 4-H | 6-H | 5 | H | 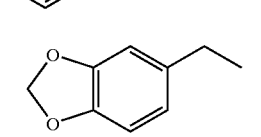 | ok |
| 175 | Phenyl-2,4-Cl$_2$ | H | H | 2-OCH$_3$ | 3-H | 4-H | 6-H | 5 | H | 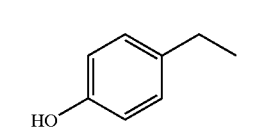 | ok |
| 176 | Phenyl-2,4-Cl$_2$ | H | H | 2-OCH$_3$ | 3-H | 4-H | 6-H | 5 | H | (CH$_2$)$_2$—COOH | ok |
| 177 | Phenyl-2,4-Cl$_2$ | H | H | 2-OCH$_3$ | 3-H | 4-H | 6-H | 5 | H | (CH$_2$)$_3$—COOH | ok |
| 178 | Phenyl-2-Cl | H | H | 2-OCH$_3$ | 3-H | 4-H | 6-H | 5 | H | 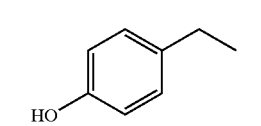 | ok |
| 179 | Phenyl-2,4-Cl$_2$ | H | H | 2-OCH$_3$ | 3-H | 4-H | 6-H | 5 | H | 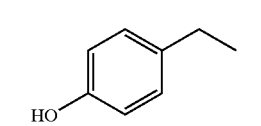 | ok |

TABLE 1-continued

Examples

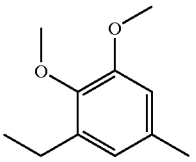

| Ex. | A | R1* | R2 | R3 | R4 | R6 | R5 | Amide | R7 | R8* | MS**** |
|---|---|---|---|---|---|---|---|---|---|---|---|
| 180 | Phenyl-2,4-Cl$_2$ | H | H | 2-OCH$_3$ | 3-H | 4-H | 6-H | 5 | H | 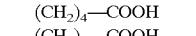 | ok |
| 181 | Phenyl-2,4-Cl$_2$ | H | H | 2-OCH$_3$ | 3-H | 4-H | 6-H | 5 | H | (CH$_2$)$_4$—COOH | ok |
| 182 | Phenyl-2,4-Cl$_2$ | H | H | 2-OCH$_3$ | 3-H | 4-H | 6-H | 5 | H | (CH$_2$)$_5$—COOH | ok |
| 183 | Phenyl-2-Cl | H | H | 2-OCH$_3$ | 3-H | 4-H | 6-H | 5 | H | 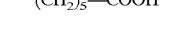 | ok |
| 184 | Phenyl-2-Cl | H | H | 2-OCH$_3$ | 3-H | 4-H | 6-H | 5 | H | (CH$_2$)$_4$—COOH | ok |
| 185 | Phenyl-2,4-Cl$_2$ | H | H | 2-OCH$_3$ | 3-H | 4-H | 6-H | 5 | H | 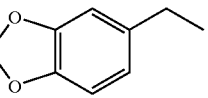 | ok |
| 186 | Phenyl-2,4-Cl$_2$ | H | H | 2-OCH$_3$ | 3-H | 4-H | 6-H | 5 | H | 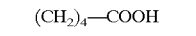 | ok |
| 187 | Phenyl-2-Cl | H | H | 2-NO$_2$ | 3-H | 5-H | 6-H | 4 | H | (CH$_2$)$_5$—OH | ok |
| 188 | Phenyl-2-Cl | H | H | 2-NO$_2$ | 3-H | 5-H | 6-H | 4 | H | (CH$_2$)$_6$—OH | ok |
| 189 | Phenyl-2-Cl | H | H | 2-NO$_2$ | 3-H | 5-H | 6-H | 4 | H | 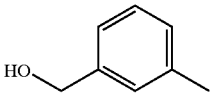 | ok |
| 190 | Phenyl-2-Cl | H | H | 2-NO$_2$ | 3-H | 5-H | 6-H | 4 | H | 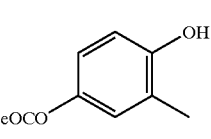 | ok |
| 191 | Phenyl-2-Cl | H | H | 2-NO$_2$ | 3-H | 5-H | 6-H | 4 | H | 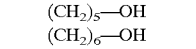 | ok |
| 192 | Phenyl-2-Cl | H | H | 2-NO$_2$ | 3-H | 5-H | 6-H | 4 | H |  | ok |
| 193 | Phenyl-2-Cl | H | H | 2-NO$_2$ | 3-H | 5-H | 6-H | 4 | H |  | ok |

TABLE 1-continued
Examples
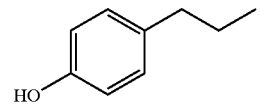
| Ex. | A | R1* | R2 | R3 | R4 | R6 | R5 | Amide | R7 | R8* | MS**** |
|---|---|---|---|---|---|---|---|---|---|---|---|
| 194 | Phenyl-2-Cl | H | H | 2-NO$_2$ | 3-H | 5-H | 6-H | 4 | H | 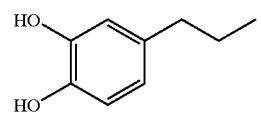 | ok |
| 195 | Phenyl-2-Cl | H | H | 2-NO$_2$ | 3-H | 5-H | 6-H | 4 | H | 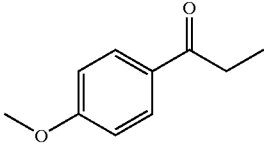 | ok |
| 196 | Phenyl-2-Cl | H | H | 2-NO$_2$ | 3-H | 5-H | 6-H | 4 | H | 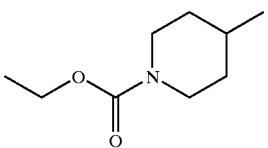 | ok |
| 197 | Phenyl-2-Cl | H | H | 2-H | 3-Cl | 5-H | 6-H | 4 | H | 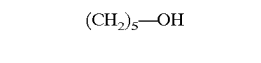 | ok |
| 198 | Phenyl-2-Cl | H | H | 2-H | 3-Cl | 5-H | 6-H | 4 | H | (CH$_2$)$_5$—OH | ok |
| 199 | Phenyl-2-Cl | H | H | 2-H | 3-Cl | 5-H | 6-H | 4 | H | 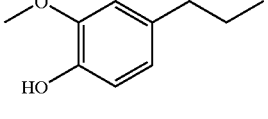 | ok |
| 200 | Phenyl-2-Cl | H | H | 2-H | 3-Cl | 5-H | 6-H | 4 | H | 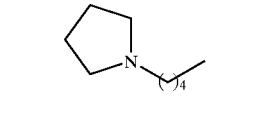 | ok |
| 201 | Phenyl-2-Cl | H | H | 2-H | 3-H | 5-H | 6-H | 4 | H | (CH$_2$)$_5$—OH | ok |
| 202 | Phenyl-2-Cl | H | H | 2-H | 3-H | 5-H | 6-H | 4 | H | (CH$_2$)$_6$—OH | ok |
| 203 | Phenyl-2-Cl | H | H | 2-H | 3-H | 5-H | 6-H | 4 | H | 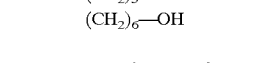 | ok |
| 204 | Phenyl-2-Cl | H | H | 2-H | 3-H | 5-H | 6-H | 4 | H | 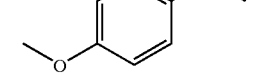 | ok |
| 205 | Phenyl-2-Cl | H | H | 2-H | 3-H | 5-H | 6-H | 4 | H | 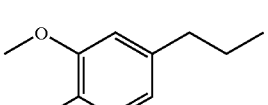 | ok |

TABLE 1-continued

Examples

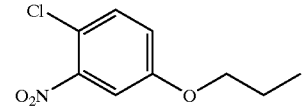

| Ex. | A | R1* | R2 | R3 | R4 | R6 | R5 | Amide | R7 | R8* | MS**** |
|---|---|---|---|---|---|---|---|---|---|---|---|
| 206 | Phenyl-2-Cl | H | H | 2-H | 3-H | 5-H | 6-H | 4 | H | 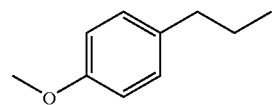 | ok |
| 207 | Phenyl-2-Cl | H | H | 2-H | 3-H | 5-H | 6-H | 4 | H | 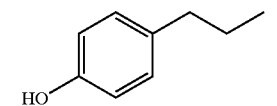 | ok |
| 208 | Phenyl-2-Cl | H | H | 2-H | 3-H | 5-H | 6-H | 4 | H | 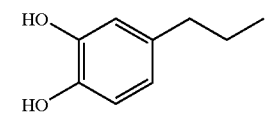 | ok |
| 209 | Phenyl-2-Cl | H | H | 2-H | 3-H | 5-H | 6-H | 4 | H | 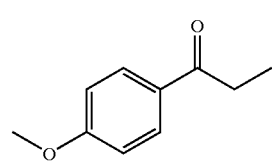 | ok |
| 210 | Phenyl-2-Cl | H | H | 2-H | 3-H | 5-H | 6-H | 4 | H | 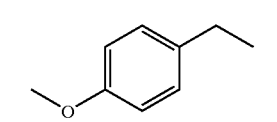 | ok |
| 211 | Phenyl-2-Cl | H | H | 2-Cl | 3-H | 5-H | 6-Cl | 4 | H | $(CH_2)_6$—OH | ok |
| 212 | Phenyl-2-Cl | H | H | 2-Cl | 3-H | 5-H | 6-Cl | 4 | H | $(CH_2)_5$—OH | ok |
| 213 | Phenyl-2-Cl | H | H | 2-Cl | 3-H | 5-$OCH_3$ | 6-H | 4 | H | $(CH_2)_5$—OH | ok |
| 214 | Phenyl-2-Cl | H | H | 2-Cl | 3-H | 5-$OCH_3$ | 6-H | 4 | H | $(CH_2)_6$—OH | ok |
| 215 | Phenyl-2-Cl | H | H | 2-Cl | 3-H | 5-$OCH_3$ | 6-H | 4 | H | 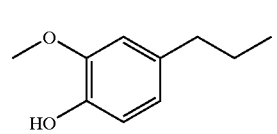 | ok |
| 216 | Phenyl-2-Cl | H | H | 2-Cl | 3-H | 5-$OCH_3$ | 6-H | 4 | H | 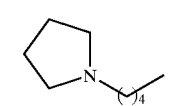 | ok |
| 217 | Phenyl-2-Cl | H | H | 2-Cl | 3-H | 5-$OCH_3$ | 6-H | 4 | H | 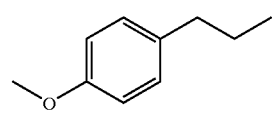 | ok |
| 218 | Phenyl-2-Cl | H | H | 2-Cl | 3-H | 5-$OCH_3$ | 6-H | 4 | H |  | ok |

TABLE 1-continued

Examples

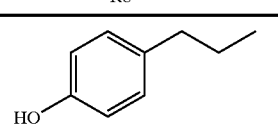

| Ex. | A | R1* | R2 | R3 | R4 | R6 | R5 | Amide | R7 | R8* | MS**** |
|---|---|---|---|---|---|---|---|---|---|---|---|
| 219 | Phenyl-2-Cl | H | H | 2-Cl | 3-H | 5-OCH$_3$ | 6-H | 4 | H | 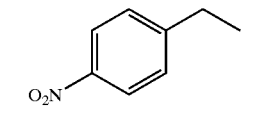 | ok |
| 220 | Phenyl-2-Cl | H | H | 2-NO$_2$ | 3-H | 5-H | 6-H | 4 | H | 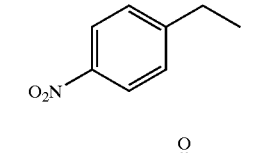 | ok |
| 221 | Phenyl-2-Cl | H | H | 2-H | 3-H | 5-H | 6-H | 4 | H | 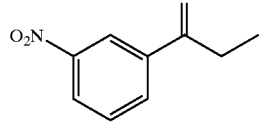 | ok |
| 222 | Phenyl-2-Cl | H | H | 2-H | 3-H | 5-H | 6-H | 4 | H | 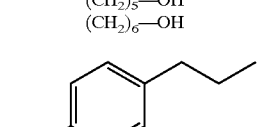 | ok |
| 223 | Phenyl-2-Cl | H | H | 2-OCH$_3$ | 3-H | 5-H | 6-H | 4 | H | (CH$_2$)$_5$—OH | ok |
| 224 | Phenyl-2-Cl | H | H | 2-OCH$_3$ | 3-H | 5-H | 6-H | 4 | H | (CH$_2$)$_6$—OH | ok |
| 225 | Phenyl-2-Cl | H | H | 2-OCH$_3$ | 3-H | 5-H | 6-H | 4 | H | 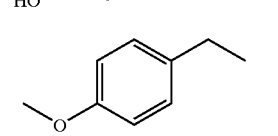 | ok |
| 226 | Phenyl-2-Cl | H | H | 2-OCH$_3$ | 3-H | 5-H | 6-H | 4 | H | 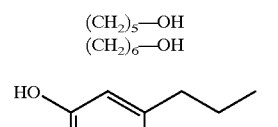 | ok |
| 227 | Phenyl-2-Cl | H | H | 2-Cl | 3-H | 5-H | 6-H | 4 | H | (CH$_2$)$_5$—OH | ok |
| 228 | Phenyl-2-Cl | H | H | 2-Cl | 3-H | 5-H | 6-H | 4 | H | (CH$_2$)$_6$—OH | ok |
| 229 | Phenyl-2-Cl | H | H | 2-Cl | 3-H | 5-H | 6-H | 4 | H | 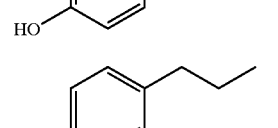 | ok |
| 230 | Phenyl-2-Cl | H | H | 2-Cl | 3-H | 5-H | 6-H | 4 | H | 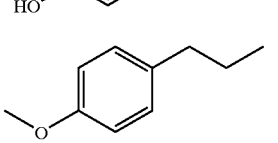 | ok |
| 231 | Phenyl-2-Cl | H | H | 2-Cl | 3-H | 5-H | 6-H | 4 | H | 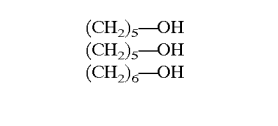 | ok |
| 232 | Phenyl-2-Cl | H | H | 2-F | 3-F | 5-F | 6-F | 4 | H | (CH$_2$)$_5$—OH | ok |
| 233 | Phenyl-2,4-Cl$_2$ | H | H | 2-OCH$_3$ | 3-H | 5-H | 6-H | 4 | H | (CH$_2$)$_5$—OH | ok |
| 234 | Phenyl-2,4-Cl$_2$ | H | H | 2-OCH$_3$ | 3-H | 5-H | 6-H | 4 | H | (CH$_2$)$_6$—OH | ok |

TABLE 1-continued
Examples
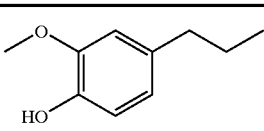
| Ex. | A | R1* | R2 | R3 | R4 | R6 | R5 | Amide | R7 | R8* | MS**** |
|---|---|---|---|---|---|---|---|---|---|---|---|
| 235 | Phenyl-2,4-Cl$_2$ | H | H | 2-OCH$_3$ | 3-H | 5-H | 6-H | 4 | H | 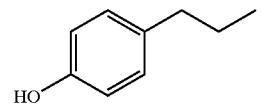 | ok |
| 236 | Phenyl-2,4-Cl$_2$ | H | H | 2-OCH$_3$ | 3-H | 5-H | 6-H | 4 | H | 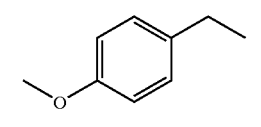 | ok |
| 237 | Phenyl-2,4-Cl$_2$ | H | H | 2-OCH$_3$ | 3-H | 5-H | 6-H | 4 | H | 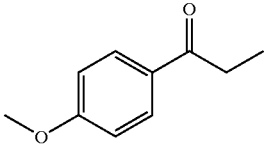 | ok |
| 238 | Phenyl-2,4-Cl$_2$ | H | H | 2-OCH$_3$ | 3-H | 5-H | 6-H | 4 | H | 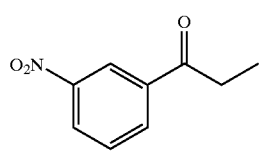 | ok |
| 239 | Phenyl-2,4-Cl$_2$ | H | H | 2-OCH$_3$ | 3-H | 5-H | 6-H | 4 | H | 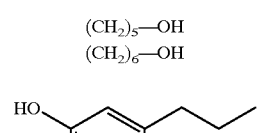 | ok |
| 240 | Phenyl-2,4-Cl$_2$ | H | H | 2-Cl | 3-H | 5-H | 6-H | 4 | H | (CH$_2$)$_5$—OH | ok |
| 241 | Phenyl-2,4-Cl$_2$ | H | H | 2-Cl | 3-H | 5-H | 6-H | 4 | H | (CH$_2$)$_6$—OH | ok |
| 242 | Phenyl-2,4-Cl$_2$ | H | H | 2-Cl | 3-H | 5-H | 6-H | 4 | H | 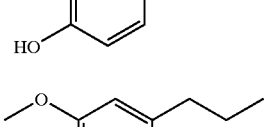 | ok |
| 243 | Phenyl-2,4-Cl$_2$ | H | H | 2-Cl | 3-H | 5-H | 6-H | 4 | H | 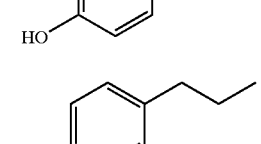 | ok |
| 244 | Phenyl-2,4-Cl$_2$ | H | H | 2-Cl | 3-H | 5-H | 6-H | 4 | H | 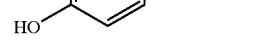 | ok |
| 245 | Phenyl-2,4-Cl$_2$ | H | H | 2-Cl | 3-H | 5-H | 6-H | 4 | H | 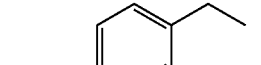 | ok |

TABLE 1-continued
Examples
| Ex. | A | R1* | R2 | R3 | R4 | R6 | R5 | Amide | R7 | R8* | MS**** |
|---|---|---|---|---|---|---|---|---|---|---|---|
| 246 | Phenyl-2,4-Cl$_2$ | H | H | 2-Cl | 3-H | 5-H | 6-H | 4 | H | 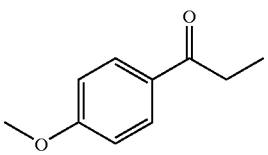 | ok |
| 247 | Phenyl-2,4-Cl$_2$ | H | H | 2-Cl | 3-H | 5-H | 6-H | 4 | H | 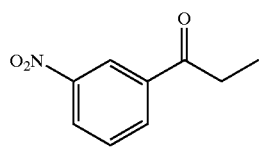 | ok |
| 248 | Phenyl-2,4-Cl$_2$ | H | H | 2-OH | 3-H | 5-H | 6-H | 4 | H | (CH$_2$)$_6$—OH | ok |
| 249 | Phenyl-2,4-Cl$_2$ | H | H | 2-NO$_2$ | 3-H | 5-H | 6-H | 4 | H | 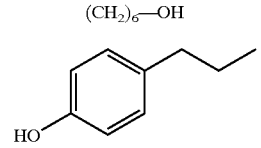 | ok |
| 250 | Phenyl-2-Cl | H | H | 2-OCH$_3$ | 3-H | 5-H | 6-H | 4 | H | 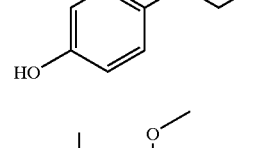 | ok |
| 251 | Phenyl-2,4-Cl$_2$ | H | H | 2-OCH$_3$ | 3-H | 5-H | 6-H | 4 | H | 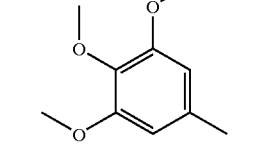 | ok |
| 252 | Phenyl-2-Cl | H | H | 2-Cl | 3-H | 5-H | 6-H | 4 | H | 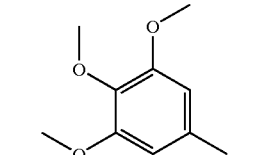 | ok |
| 253 | Phenyl-2,4-Cl$_2$ | H | H | 2-Cl | 3-H | 5-H | 6-H | 4 | H | 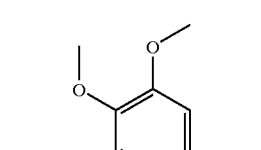 | ok |
| 254 | Phenyl-2,4-Cl$_2$ | H | H | 2-OCH$_3$ | 3-H | 4-H | 6-H | 5 | H | 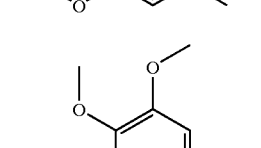 | ok |

TABLE 1-continued

Examples

| Ex. | A | R1* | R2 | R3 | R4 | R6 | R5 | Amide | R7 | R8* | MS**** |
|---|---|---|---|---|---|---|---|---|---|---|---|
| 255 | Phenyl-2-Cl-4-F | H | H | 2-OCH$_3$ | 3-H | 5-H | 6-H | 4 | H | H | ok |
| 256 | Phenyl-2,4-Cl$_2$ | H | H | 2-OCH$_3$ | 3-H | 5-H | 6-H | 4 | H | H | ok |
| 257 | Phenyl-2-Cl-4-F | H | H | 2-OCH$_3$ | 3-H | 5-H | 6-H | 4 | H | CH$_3$ | ok |
| 258 | Phenyl-2,4-Cl$_2$ | H | H | 2-OCH$_3$ | 3-H | 5-H | 6-H | 4 | H | CH$_3$ | ok |
| 259 | Phenyl-2-Cl-4-F | H | H | 2-OCH$_3$ | 3-H | 5-H | 6-H | 4 | H | (CH$_2$)$_3$—NHCOO—CH$_2$—Ph | ok |
| 260 | Phenyl-2-Cl-4,5-F$_2$ | H | H | 2-OCH$_3$ | 3-H | 5-H | 6-H | 4 | H | (CH$_2$)$_3$—NHCOO—CH$_2$—Ph | ok |
| 261 | Phenyl-2-Cl-4-F | H | H | 2-OCH$_3$ | 3-H | 5-H | 6-H | 4 | CH$_3$ | CH$_3$ | ok |
| 262 | Phenyl-2,4-Cl$_2$ | H | H | 2-OCH$_3$ | 3-H | 5-H | 6-H | 4 | CH$_3$ | CH$_3$ | ok |
| 263 | Phenyl-2-Cl-4,5-F$_2$ | H | H | 2-OCH$_3$ | 3-H | 5-H | 6-H | 4 | H | CH$_3$ | ok |
| 264 | Phenyl-2-Cl-4,5-F$_2$ | H | H | 2-OCH$_3$ | 3-H | 5-H | 6-H | 4 | CH$_3$ | CH$_3$ | ok |
| 265 | Phenyl-2-Cl-4,5-F$_2$ | H | H | 2-OCH$_3$ | 3-H | 5-H | 6-H | 4 | H | (CH$_2$)$_2$—NHCO—CH$_3$ | ok |
| 266 | Phenyl-2-Cl-4,5-F$_2$ | H | H | 2-OCH$_3$ | 3-H | 5-H | 6-H | 4 | H | (CH$_2$)$_3$—NH$_2$ TFA | ok |
| 267 | Phenyl-2-Cl-4,5-F$_2$ | H | H | 2-Cl | 3-H | 5-H | 6-H | 4 | H | CH$_3$ | ok |
| 268 | Phenyl-2-Cl-4,5-F$_2$ | H | H | 2-Cl | 3-H | 5-H | 6-H | 4 | CH$_3$ | CH$_3$ | ok |
| 269 | Phenyl-2-Cl-4,5-F$_2$ | H | H | 2-Cl | 3-H | 5-H | 6-H | 4 | H | H | ok |
| 270 | Phenyl-2-Cl-4,5-F$_2$ | H | H | 2-OCH$_3$ | 3-H | 5-H | 6-H | 4 | H | (CH$_2$)$_3$—N(CH$_3$)$_2$ TFA | ok |
| 271 | Phenyl-2-Cl-4,5-F$_2$ | H | H | 2-OCH$_3$ | 3-H | 5-H | 6-H | 4 | H | (CH$_2$)$_2$—N(CH$_3$)$_2$ TFA | ok |
| 272 | Phenyl-2,4-Cl$_2$ | H | H | 2-Cl | 3-H | 5-H | 6-H | 4 | H | (CH$_2$)$_2$—NHCOO—CH$_2$—CH=CH$_2$ | ok |
| 273 | Phenyl-2-Cl-4,5-F$_2$ | H | H | 2-OCH$_3$ | 3-H | 5-H | 6-H | 4 | H | (CH$_2$)$_4$—NH$_2$ TFA | ok |
| 274 | Phenyl-2,4-Cl$_2$ | H | H | 2-Cl | 3-H | 5-H | 6-H | 4 | H | (CH$_2$)$_2$—NH$_2$ TFA | ok |
| 275 | Phenyl-2-Cl-4-F | H | H | 2-OCH$_3$ | 3-H | 5-H | 6-H | 4 | H | (CH$_2$)$_3$—NH$_2$ TFA | ok |
| 276 | Phenyl-2-Cl-4,5-F$_2$ | H | H | 3-H | 4-H | 5-COOH | 6-H | 2 | H | CH$_3$ | ok |
| 277 | Phenyl-2-Cl-4,5-F$_2$ | H | H | 2-OCF$_3$ | 3-H | 5-H | 6-H | 4 | H | CH$_3$ | ok |
| 278 | Phenyl-2-Cl-4,5-F$_2$ | H | H | 2-OCF$_3$ | 3-H | 5-H | 6-H | 4 | CH$_3$ | CH$_3$ | ok |
| 279 | Phenyl-2-Cl-4,5-F$_2$ | H | H | 3-H | 4-H | 5-H | 6-H | 2 | H | H | ok |
| 280 | Phenyl-2-Cl-4,5-F$_2$ | H | H | 2-OCF$_3$ | 3-H | 5-H | 6-H | 4 | H | CH$_2$—COO—CH$_3$ | ok |
| 281 | Phenyl-2-Cl-4,5-F$_2$ | H | H | 2-OCF$_3$ | 3-H | 5-H | 6-H | 4 | CH$_3$ | CH$_2$—COO—CH$_3$ | ok |
| 282 | Phenyl-2-Cl-4,5-F$_2$ | H | H | 2-OCF$_3$ | 3-H | 5-H | 6-H | 4 | H | (CH$_2$)$_2$—COO—CH$_3$ | ok |
| 283 | Phenyl-2-Cl-4,5-F$_2$ | H | H | 2-OCF$_3$ | 3-H | 5-H | 6-H | 4 | H | (CH$_2$)$_3$—COO—CH$_3$ | ok |
| 284 | Phenyl-2-Cl-4,5-F$_2$ | H | H | 2-OCF$_3$ | 3-H | 5-H | 6-H | 4 | H | CH$_2$—COOH | ok |
| 285 | Phenyl-2-Cl-4,5-F$_2$ | H | H | 2-OCF$_3$ | 3-H | 5-H | 6-H | 4 | CH$_3$ | CH$_2$—COOH | ok |
| 286 | Phenyl-2-Cl-4,5-F$_2$ | H | H | 2-OCF$_3$ | 3-H | 5-H | 6-H | 4 | H | (CH$_2$)$_2$—COOH | ok |
| 287 | Phenyl-2-Cl-4,5-F$_2$ | H | H | 2-OCF$_3$ | 3-H | 5-H | 6-H | 4 | H | (CH$_2$)$_3$—COOH | ok |

*"Na" means the sodium salt of the corresponding compound with R1 = H
**In the "Amide" column, the position of the carboxamide group —(C=O)—N(R7)(R8) on the phenyl radical is indicated.
***Where structural formulae are indicated for R8, the bonding of R8 to the nitrogen takes place via the short depicted bond
****The statement "MS is ok" means that a mass spectrum was measured and, in this, the molecular peak (molecular mass + H$^+$) was detected.

The compounds of the formula I are distinguished by beneficial effects on glucose metabolism; in particular they lower the blood glucose level and are suitable for treating type II diabetes. The compounds can be employed alone or in combination with other blood glucose-lowering active ingredients (antidiabetics). Examples of such blood glucose-lowering active ingredients are sulfonylureas (such as, for example, glimepiride, glibenclamide, gliclazide, glibornuride, gliquidone, glisoxepide), metformin, tolbutamide, glitazones (such as, for example, troglitazone, rosiglitazone, pioglitazone, repaglinide), alpha-glucosidase inhibitors (such as, for example, acarbose, miglitol) or insulins. All antidiabetics mentioned in chapter 12 of the Rote Liste 2001 can be combined with the compounds of the formula I of the invention for improving the effect. Administration of the active ingredient combination can take place either by separate administration of the active ingredients to the patients or in the form of combination products in which a plurality of active ingredients are present in one pharmaceutical preparation.

The compounds of the formula I are additionally suitable for the treatment of late complications of diabetes such as, for example, nephropathy, retinopathy, neuropathy and myocardial infarction, peripheral arterial occlusive diseases, thromboses, arteriosclerosis, syndrome X, obesity, inflammations, immune diseases, autoimmune diseases such as, for example, AIDS, asthma, osteoporosis, cancer, psoriasis, Alzheimer's, schizophrenia and infectious diseases.

The activity of the compounds was assayed as follows:

Glycogen Phosphorylase a Activity Assay

The effect of compounds on the activity of the active form of glycogen phosphorylase (GPa) was measured in the reverse direction by following the synthesis of glycogen from glucose 1-phosphate by determining the liberation of inorganic phosphate. All the reactions were carried out as duplicate determinations in microtiter plates with 96 wells (Half Area Plates, Costar No 3696), measuring the change in absorption owing to the formation of the reaction product at the wavelength specified hereinafter in a Multiskan Ascent Elisa Reader (Lab Systems, Finland). In order to measure the GPa enzymic activity in the reverse direction, the general method of Engers et al. (Engers HD, Shechosky S, Madsen NB, Can J Biochem July 1970;48(7):746–754) was used to measure the conversion of glucose 1-phosphate into glycogen and inorganic phosphate, with the following modifications: human glycogen phosphorylase a (for example with 0.76 mg of protein/ml (Aventis Pharma Deutschland GmbH), dissolved in buffer solution E (25 mM β-glycerophosphate, pH 7.0,1 mM EDTA and 1 mM dithiothreitol) was diluted with buffer T (50 mM Hepes, pH 7.0, 100 mM KCl, 2.5 mM EDTA, 2.5 mM $MgCl_2 \cdot 6H_2O$) and addition of 5 mg/ml glycogen to a concentration of 10 μg of protein/ml. Test substances were prepared as 10 mM solution in DMSO and diluted to 50 μM with buffer solution T. To 10 μl of this solution were added 10 μl of 37.5 mM glucose, dissolved in buffer solution T, and 5 mg/ml glycogen, plus 10 μl of a solution of human glycogen phosphorylase a (10 μg of protein/ml) and 20 μl of glucose 1-phosphate, 2.5 mM. The baseline glycogen phosphorylase a activity in the absence of test substance was determined by adding 10 μl of buffer solution T (0.1% DMSO). The mixture was incubated at room temperature for 40 minutes, and the liberated inorganic phosphate was measured by the general method of Drueckes et al. (Drueckes P, Schinzel R, Palm D, *Anal Biochem* 1995 Sep. 1;230(1):173–177) with the following modifications: 50 μl of a stop solution of 7.3 mM ammonium molybdate, 10.9 mM zinc acetate, 3.6% ascorbic acid, 0.9% SDS are added to 50 μl of the enzyme mixture. After incubation at 45° C. for 60 minutes, the absorption at 820 nm was measured. To determine the background absorption, in a separate mixture the stop solution was added immediately after addition of the glucose 1-phosphate solution.

This test was carried out with a concentration of 10 μM of the test substance in order to determine the particular inhibition of glycogen phosphorylase a in vitro by the test substance.

TABLE 2

| | Biological activity: |
|---|---|
| Ex. | % inhibition at 10 μM |
| 1 | 87 |
| 2 | 73 |
| 3 | 75 |
| 4 | 79 |
| 5 | 77 |
| 12 | 92 |
| 20 | 35 |
| 29 | 78 |
| 30 | 76 |
| 31 | 86 |
| 41 | 50 |
| 44 | 11 |

TABLE 2-continued

| | Biological activity: |
|---|---|
| Ex. | % inhibition at 10 μM |
| 46 | 36 |
| 47 | 46 |
| 49 | 13 |
| 51 | 36 |
| 53 | 22 |
| 60 | 36 |
| 70 | 86 |
| 75 | 41 |
| 80 | 50 |
| 84 | 44 |
| 89 | 90 |
| 90 | 34 |
| 100 | 78 |
| 101 | 93 |
| 102 | 14 |
| 106 | 35 |
| 111 | 88 |
| 112 | 100 |
| 116 | 100 |
| 117 | 99 |
| 118 | 70 |
| 119 | 97 |
| 120 | 40 |
| 122 | 12 |
| 128 | 95 |
| 147 | 88 |
| 149 | 76 |

It is to be inferred from the table that the compounds of the formula I inhibit the activity of glycogen phosphorylase a and are thus very suitable for lowering the blood glucose level.

The preparation of some examples is described in detail below, and the other compounds of the formula I were obtained analogously: Experimental Part:

EXAMPLE 1 a) 2-Chlorobenzoyl Isocyanate

2-Chlorobenzamide was dissolved in dichloromethane, mixed with 1.5 eq. of oxalyl chloride and heated to reflux for 16 hours. The reaction mixture was concentrated under high vacuum and reacted in stage b without further purification.

b) 4-Chloro-3-[3-(2-chlorobenzoyl)ureido]benzoic acid 1 g (5.8 mmol) of 3-amino-4-chlorobenzoic acid were mixed with 0.75 g (5.8 mmol) of diisopropylethylamine and 1.06 g (5.8 mmol) of 2-chlorobenzoyl isocyanate in 5 ml of dichloromethane and reacted at room temperature for 12 hours. The solvent was evaporated, the residue was mixed with 5% strength sodium bicarbonate solution and extracted twice with diethyl ether, and the aqueous phase was adjusted to pH 3 with HCl. The resulting precipitate was filtered off with suction.

c) Ethyl 4-{4-chloro-3-[3-(2-chlorobenzoyl)ureido]benzoylamino}piperidine-1-carboxylate 100 mg (0.28 mmol) of 4-chloro-3-[3-(2-chlorobenzoyl)ureido]benzoic acid, 93 mg (0.28 mmol) of TOTU and 37 mg (0.28 mmol) of diisopropylethylamine were coupled in 1 ml of dimethylformamide. The reaction solution was washed once each with 5% strength sodium bicarbonate solution and 10% strength citric acid solution, and the organic phase was dried and concentrated.

EXAMPLES 2–52 AND 188–220 WERE SYNTHESIZED IN ANALOGY TO EXAMPLE 1

EXAMPLE 94 a) 4-[3-(2,4-Dichlorobenzoyl)ureido]-3-methoxybenzoic acid 36.1 g (167.5 mmol) of 2,4-dichlorobenzoyl isocyanate, which was prepared in analogy to example 1a, were added to a solution of 20 g (119.6 mmol) of 4-amino-3-methoxybenzoic acid in 400 ml of acetonitrile. The mixture was heated to reflux for 2 hours and cooled to room temperature. The precipitate was filtered off with suction, washed with acetonitrile and methanol, stirred with 5% strength potassium bisulfate solution, again filtered off with suction and dried under high vacuum. 44 g (96%) of the desired product were obtained.

b) 4-[3-(2,4-Dichlorobenzoyl)ureido]-3-methoxybenzoyl chloride 11.25 g (37.2 mmol) of 4-[3-(2,4-dichlorobenzoyl)ureido]-3-methoxybenzoic acid from stage a were heated to reflux with 150 ml of thionyl chloride for 3 hours and evaporated in a rotary evaporator under high vacuum. The residue was twice mixed with toluene and again evaporated under high vacuum to result in 10.88 g (27.09 mmol, 73%) of acid chloride (loss due to foaming over). The product obtained in this way was employed in the next stage without further purification.

c) 3-[3-(2,4-Dichlorobenzoyl)ureido]-4-methoxy-N-(2,2,6,6-tetramethylpiperidin-4-yl)benzamide Sodium Salt A suspension of 157 mg (0.39 mmol) of acid chloride from stage b and 4 ml of dichloromethane was added to a solution of 65 µl (0.8 mmol) of pyridine and 63 mg (0.4 mmol) of 2,2,6,6-tetramethylpiperidin-4-ylamine in 2 ml of dichloromethane, and the reaction mixture was reacted at room temperature for 16 hours. The reaction mixture was diluted with 2.5 ml of acetonitrile, filtered and washed with 5 ml of acetonitrile, and the filtrate was evaporated. The residue was taken up in a mixture of 2N of sodium hydroxide solution, acetonitrile and dimethylformamide (1/2/2), whereupon the product precipitated.

Examples 95–152 were synthesized in analogy to example 94. If required, the products were purified by preparative reverse phase HPLC (acetonitrile/water/TFA).

We claim:

1. A compound of the formula I,

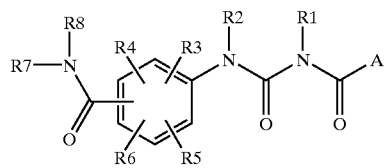

I in which

A is phenyl or naphthyl, where the phenyl or naphthyl is unsubstituted or substituted 1, 2, or 3 times wherein each substituent is independently chosen from F, Cl, Br, OH, $CF_3$, $NO_2$, CN, $OCF_3$, O—$(C_1$–$C_6)$-alkyl, O—$(C_2$–$C_6)$-alkenyl, O—$(C_2$–$C_6)$alkynyl, S—$(C_1$–$C_6)$-alkyl, S—$(C_2$–$C_6)$-alkenyl, S—$(C_2$–$C_6)$-alkynyl, SO—$(C_1$–$C_6)$-alkyl, $SO_2$—$(C_1$–$C_6)$-alkyl, $SO_2$—$NH_2$, $(C_1$–$C_6)$-alkyl, $(C_2$–$C_6)$-alkenyl, $(C_2$–$C_6)$-alkynyl, $(C_3$–$C_7)$-cycloalkyl, $(C_3$–$C_7)$-cycloalkyl-$(C_1$–$C_4)$-alkylene, $(C_0$–$C_6)$-alkylene-COOH, $(C_0$–$C_6)$-alkylene-COO—$(C_1$–$C_7)$-alkyl, $(C_0$–$C_6)$-alkylene-COO—$(C_2$–$C_7)$-alkenyl, $CONH_2$, CONH—$(C_1$–$C_6)$-alkyl, CON—$[(C_1$–$C_6)$-alkyl]$_2$, CONH—$(C_3$–$C_6)$-cycloalkyl, $(C_0$–$C_6)$-alkylene-$NH_2$, $(C_0$–$C_6)$-alkylene-NH—$(C_2$–$C_6)$-alkyl, $(C_0$–$C_6)$-alkylene-N—$[(C_1$–$C_6)$-alkyl]$_2$, NH—CO—$(C_1$–$C_6)$-alkyl, NH—CO-phenyl, and NH—$SO_2$-phenyl, wherein the phenyl of NH—CO-phenyl and and NH—$SO_2$-phenyl is unsubstituted or substituted 1 or 2 times wherein each substituent is independently chosen from F, Cl, CN, OH, $(C_1$–$C_6)$-alkyl, O—$(C_1$–$C_6)$-alkyl, $CF_3$, $OCF_3$, COOH, COO—$C_1$–$C_6)$-alkyl and $CONH_2$;

R1, R2 are, independently of one another, H, $(C_1$–$C_6)$-alkyl, O—$(C_1$–$C_6)$-alkyl, CO—$(C_1$–$C_6)$-alkyl or COO—$(C_1$–$C_6)$-alkyl;

R3, R4, R5, R6 are, independently of one another, H, F, Cl, Br, OH, $CF_3$, $NO_2$, CN, $OCF_3$, O—$(C_1$–$C_6)$-alkyl, O—$(C_2$–$C_6)$-alkynyl, O—$(C_2$–$C_6)$-alkynyl, S—$(C_1$–$C_6)$-alkyl, S—$(C_2$–$C_6)$-alkenyl, S—$(C_2$–$C_6)$-alkynyl, SO—$(C_1$–$C_6)$-alkyl, $SO_2$—$(C_1$–$C_6)$-alkyl, $SO_2$—$NH_2$, $(C_1$–$C_6)$-alkyl, $(C_2$–$C_6)$-alkenyl, $(C_2$–$C_6)$-alkynyl, $(C_3$–$C_7)$-cycloalkyl, $(C_3$–$C_7)$-cycloalkyl-$(C_1$–$C_4)$-alkylene, COOH, COO—$(C_1$–$C_6)$-alkyl, CO—$NH_2$, CO—NH—$(C_1$–$C_6)$-alkyl, CO—N—$[(C_1$–$C_6)$-alkyl]$_2$, CO—NH—$(C_3$–$C_7)$-cycloalkyl, $NH_2$, NH—$(C_1$–$C_6)$-alkyl, N—$[(C_1$–$C_6)$-alkyl]$_2$, NH—CO—$(C_1$–$C_6)$-alkyl, NH—CO-phenyl, or NH—$SO_2$-phenyl, wherein the phenyl of NH—CO-phenyl and NH—$SO_2$-phenyl is unsubstituted or substituted 1 or 2 times wherein each substituent is independently chosen from F, Cl, CN, OH, $(C_1$–$C_6)$-alkyl, O—$(C_1$–$C_6)$-alkyl, $CF_3$, $OCF_3$, COOH, COO—$(C_1$–$C_6)$-alkyl and CO—$NH_2$;

R7 is H, $(C_1$–$C_6)$-alkyl, or CO($(C_1$–$C_6)$-alkyl;

R8 is H, $(C_1$–$C_{10})$-alkyl, where the alkyl is unsubstituted or substituted 1, 2, or 3 times wherein each substituent is independently chosen from OH, $CF_3$, CN, COOH, COO—$(C_1$–$C_6)$-alkyl, CO—$NH_2$, $NH_2$, NH—$(C_1$–$C_6)$-alkyl, N—$[(C_1$–$C_6)$-alkyl]$_2$, NCO—$(C_1$–$C_6)$-alkyl, NCOO—$(C_1$–$C_6)$-alkyl, NCOO—$(C_1$–$C_6)$-alkenyl, NCOO—$(C_1$–$C_6)$-alkenyl and NCOO—$(C_1$–$C_4)$-alkylene-$(C_6$–$C_{10})$-aryl; or $(CH_2)_m$-aryl, where m ranges from 0–6, and aryl is phenyl, O-phenyl, CO-phenyl, tetrahydronaphthyl or naphthyl, where the aryl is unsubstituted or substituted by at least one R9;

R9 is F, Cl, Br; OH, $NO_2$, $CF_3$, $OCF_3$, $(C_1$–$C_6)$-alkyl, $(C_1$–$C_6)$-alkyl-OH, O—$(C_1$–$C_6)$-alkyl, S—$(C_1$–$C_6)$-alkyl, $(C_1$–$C_4)$-alkylphenyl, COOH, or COO—$(C_1$–$C_6)$-alkyl;

or a physiologically tolerable salt thereof, in any stereoisomeric form[, or a mixture of any such compounds in any ratio].

2. The compound as claimed in claim 1, in which

A is phenyl, where the phenyl Is unsubstituted or substituted 1, 2, or 3 times wherein each substituent is independently chosen from F, Cl, and Br;

R1, R2 are H; R3, R4, R5, R6 are, independently of one another, H, F, Cl, Br, $NO_2$, O—$(C_1$–$C_6)$-alkyl, or $(C_1$–$C_6)$-alkyl;

R7 is H, or $CH_3$;

R8 is H, $(C_1$–$C_{10})$-alkyl, where alkyl is unsubstituted or substituted 1, 2, or 3 times wherein each substituent is independently chosen from OH, $CF_3$, CN, COOH, COO—$(C_1$–$C_6)$-alkyl, CO—$NH_2$, $NH_2$, NH—$(C_1$–$C_6)$-alkyl, N—$[(C_1$–$C_6)$-alkyl]$_2$, NCO—$C_1$–$C_6)$-alkyl, NCOO—$(C_1$–$C_6)$-alkyl, NCOO—$(C_1$–$C_6)$-alkenyl, NCOO—$(C_1$–$C_6)$-alkynyl or NCOO—$(C_1$–$C_4)$-alkylene-$(C_6$–$C_{10})$-aryl; or $(CH_2)_m$-aryl, where m ranges from 0–6, and aryl is phenyl, O-phenyl, CO-phenyl, tetrahydronaphthyl or naphthyl, where the aryl is unsubstituted or substituted by at least one R9;

R9 is F, Cl, Br, OH, $NO_2$, $CF_3$, $OCF_3$, $(C_1-C_6)$-alkyl, $(C_1-C_6)$-alkyl-OH, O—$(C_1-C_6)$-alkyl, S—$(C_1-C_6)$-alkyl, $(C_1-C_4)$-alkylphenyl, COOH, or COO—$(C_1-C_6)$-alkyl;

or a pharmaceutically tolerable salt thereof, in any stereoisomeric form[, or a mixture of any such compounds in any ratio].

3. The compound as claimed in claim 1, in which

A is phenyl, where the phenyl is unsubstituted or substituted 1, 2, or 3 times wherein each substituent is independently chosen from F, Cl, and Br;

R1, R2 are H;

R3, R4, R5, R6 are, independently of one another, H, F, Cl, Br, $NO_2$, O—$(C_1-C_6)$-alkyl, or $(C_1-C_6)$-alkyl;

R7 is H, or $CH_3$;

R8 is $(C_1-C_{10})$-alkyl, where the alkyl is unsubstituted or substituted 1, 2, or 3 times wherein each substituent is independently chosen from OH, $CF_3$, CN, COOH, COO—$(C_1-C_6)$-alkyl, CO—$NH_2$, $NH_2$, NH—$(C_1-C_6)$-alkyl, N—$[(C_1-C_6)$-alkyl$]_2$, NCO—$(C_1-C_6)$-alkyl, NCOO—$(C_1-C_6)$-alkyl, NCOO—$(C_1-C_6)$-alkenyl, NCOO—$(C_1-C_6)$-alkynyl or NCOO—$(C_1-C_4)$-alkylene-$(C_6-C_{10})$-aryl; or $(C_2)_m$-aryl, where m ranges from 0–6, and aryl is phenyl, O-phenyl, CO-phenyl, tetrahydronaphthyl or naphthyl, where the aryl is unsubstituted or substituted by at least one R9; is F, Cl, Br; OH, $NO_2$, $CF_3$, $OCF_3$, $(C_1-C_6)$-alkyl, $(C_1-C_6)$-alkyl-OH, O—$(C_1-C_6)$-alkyl, S—$(C_1-C_6)$-alkyl, $(C_1-C_4)$-alkylphenyl, COOH or COO—$(C_1-C_6)$-alkyl;

or a pharmaceutically tolerable salt thereof, in any stereoisomeric form[, or a mixture of any such compounds in any ratio].

4. A medicament, comprising at least one compound as claimed in claim 1 and at least one pharmaceutically acceptable carrier.

5. A method of lowering blood glucose comprising administering to a patient in need thereof an effective amount of at least one compound chosen from compounds of the formula I,

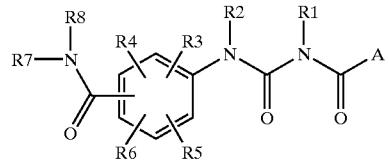

I in which

A is phenyl or naphthyl, where the phenyl or naphthyl is unsubstituted or substituted 1, 2, or 3 times wherein each substituent is independently chosen from F, Cl, Br, OH, $CF_3$, $N_2$, CN, $OCF_3$, O—$(C_1-C_6)$-alkyl, O—$(C_2-C_6)$-)-alkenyl, O—$(C_2-C_6)$-alkyl, S—$(C_1-C_6)$-alkyl, S—$(C_2-C_6)$-alkenyl, S—$(C_2-C_6)$-alkenyl, SO—$(C_1-C_6)$-alkyl, $SO_2$—$(C_1-C_6)$-alkyl, $SO_2$—$NH_2$, $(C_1-C_6)$-alkyl, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkylene, $(C_0-C_6)$-alkylene-COOH, $(C_0-C_6)$-alkylene-COO—$(C_1-C_7)$-alkyl, $(C_0-C_6)$-alkylene-COO—$(C_2-C_7)$-alkenyl, $CONH_2$, CONH—$(C_1-C_6)$-alkyl, CON—$[(C_1-C_6)]_2$, CONH—$(C_3-C_6)$cycloalkyl, $(C_0-C_6)$-alkylene-$NH_2$, $(C_0-C_6)$-alkylene-NH—$(C_2-C_6)$-alkyl, $(C_0-C_6)$-alkylene-N—$[(C_1-C_6)$-alkyl$]_2$, NH—CO—$(C_1-C_6)$-alkyl, NH—CO-phenyl, and NH—$SO_2$-phenyl, wherein the phenyl of NH—CO-phenyl and and NH—$SO_2$-phenyl is unsubstituted or substituted 1 or 2 times wherein each substituent is independently chosen from F, Cl, CN, OH, $(C_1-C_6)$-alkyl, O—$(C_1-C_6)$-alkyl, $CF_3$, $OCF_3$, COOH, COO—$(C_1-C_6)$-alkyl and $CONH_2$;

R1, R2 are, independently of one another, H, $(C_1-C_6)$-alkyl, O—$(C_{1-6})$-alkyl, CO—$(C_1-C_6)$-alkyl or COO—$(C_1-C_6)$-alkyl;

R3, R4, R5, R6 are, independently of one another, H, F, Cl, Br, OH, $CF_3$, $NO_2$, CN, $OCF_3$, O—$(C_1-C_6)$-alkyl, O—$(C_2-C_6)$-alkynyl, O—$(C_2-C_6)$-alkynyl, S—$(C_1-C_6)$-alkyl, S—$(C_2-C_6)$-alkenyl, S—$(C_2-C_6)$-alkynyl, SO—$(C_1-C_6)$-alkyl, $SO_2$—$(C_1-C_6)$-alkyl, $SO_2$—$NH_2$, $(C_1-C_6)$-alkyl, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkylene, COOH, COO—$(C_1-C_6)$-alkyl, CO—$NH_2$, CO—NH—$(C_1-C_6)$-alkyl, CO—N—$[(C_1-C_6)$-alkyl$]_2$, CO—NH—$(C_3-C_7)$-cycloalkyl, $NH_2$, NH—$(C_1-C_6)$-alkyl, N—$[(C_1-C_6)$-alkyl$]_2$, NH—CO—$(C_1-C_6)$-alkyl, NH—CO-phenyl, or NH—$SO_2$-phenyl, wherein the phenyl of NH—CO-phenyl and NH—CO-phenyl, and NH—$SO_2$-phenyl is unsubstituted or substituted 1 or 2 times wherein each substituent is independently chosen from F, Cl, CN, OH, $(C_1-C_6)$-alkyl, O—$(C_1-C_6)$-alkyl, $CF_3$, $OCF_3$, COOH, COO—$(C_1-C_6)$-alkyl and CO—$NH_2$;

R7 is H, $(C_1-C_6)$-alkyl, or $CO(C_1-C_6)$-alkyl;

R8 is H, $(C_1-C_{10})$-alkyl, where the alkyl is unsubstituted or substituted 1, 2, or 3 times wherein each substituent is independently chosen from OH, $CF_3$, CN, COOH, COO—$(C_1-C_6)$-alkyl, CO—$NH_2$, $NH_2$, NH—$(C_1-C_6)$ alkyl, N—$[(C_1-C_6)$-alkyl$]_2$, NCO—$(C_1-C_6)$-alkyl, NCOO—$(C_1-C_6)$-alkyl, NCOO—$(C_1-C_6)$-alkenyl, NCOO—$(C_1-C_6)$-alkynyl and NCOO—$(C_1-C_4)$-alkylene-$(C_5-C_{10})$-aryl; or $(CH_2)_m$-aryl, where m ranges from 0–6, and aryl is phenyl, O-phenyl, CO-phenyl, tetrahydronaphthyl or naphthyl, where the aryl is unsubstituted or substituted by at least one R9;

R9 is F, Cl, Br; OH, $NO_2$, $CF_3$, $OCF_3$, $(C_1-C_6)$-alkyl, $(C_1-C_6)$-alkyl-OH, O—$(C_1-C_6)$-alkyl, S—$(C_1-C_6)$-alkyl, $(C_1-C_4)$-alkylphenyl, COOH or COO—$(C_1-C_6)$-alkyl;

and physiologically tolerable salts thereof, in any stereoisomeric form.

6. A method for treating type II diabetes comprising administering to a patient in need thereof an effective amount of at least one compound chosen from compounds of the formula I

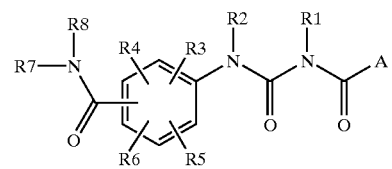

I in which

A is phenyl or naphthyl, where the phenyl or naphthyl is unsubstituted or substituted 1, 2, or 3 times wherein each substituent is independently chosen from F, Cl, Br, OH, $CF_3$, $NO_2$, CN, $OCF_3$, O—$(C_1-C_6)$-alkyl, O—($C_2$–$C_6$)-alkenyl, O—($C_2$–$C_6$)alkynyl, S—($C_1$–$C_6$)-alkyl, S—($C_2$–$C_6$)-alkenyl, S—($C_2$–$C_6$)-alkynyl, SO—($C_1$–$C_6$)-alkyl, $SO_2$—($C_1$–$C_6$)-alkyl, $SO_2$—$NH_2$, ($C_1$–$C_6$)-alkyl, ($C_2$–$C_6$)-alkenyl, ($C_2$–$C_6$)-alkynyl, ($C_3$–$C_7$)-cycloalkyl, ($C_3$–$C_7$)-cycloalkyl-($C_1$–$C_4$)-alkylene, ($C_0$–$C_6$)-alkylene-COOH, ($C_0$–$C_6$)-alkylene-COO—($C_1$–$C_7$)-alkyl, ($C_0$–$C_6$)-alkylene-COO—($C_2$–$C_7$)-alkenyl, $CONH_2$, CONH—($C_1$–$C_6$)-alkyl, CON—[($C_1$–$C_6$)-alkyl]$_2$, CONH—($C_3$–$C_6$)-cycloalkyl, ($C_0$–$C_6$)-alkylene-$NH_2$, ($C_0$–$C_6$)-alkylene-NH—($C_2$–$C_6$)-alkyl, ($C_0$–$C_6$)-alkylene-N—[($C_1$–$C_6$)-alkyl]$_2$, NH—CO—($C_1$–$C_6$)-alkyl, NH—CO-phenyl, and NH—$SO_2$-phenyl, wherein the phenyl of NH—CO-phenyl and and NH—$SO_2$-phenyl is unsubstituted or substituted 1 or 2 times wherein each substituent is independently chosen from F, Cl, CN, OH, ($C_1$–$C_6$)-alkyl, O—($C_1$–$C_6$)-alkyl, $CF_3$, $OCF_3$, COOH, COO—($C_1$–$C_6$)-alkyl and $CONH_2$;

R1, R2 are, independently of one another, H, ($C_1$–$C_6$)-alkyl, O—($C_1$–$C_6$)-alkyl, CO—($C_1$–$C_6$)-alkyl or COO—($C_1$–$C_6$)-alkyl;

R3, R4, R5, R6 are, independently of one another, H, F, Cl, Br, OH, $CF_3$, $NO_2$, CN, $OCF_3$, O—($C_1$–$C_6$)-alkyl, O—($C_2$–$C_6$)-alkenyl, O—($C_2$–$C_6$)-alkynyl, S—($C_1$–$C_6$)-alkyl, S—($C_2$–$C_6$)-alkenyl, S—($C_2$–$C_6$)-alkynyl, SO—($C_1$–$C_6$)-alkyl, $SO_2$—($C_1$–$C_6$)-alkyl, $SO_2$—$NH_2$, ($C_1$–$C_6$)-alkyl, ($C_2$–$C_6$)-alkenyl, ($C_2$–$C_6$)-alkynyl, ($C_3$–$C_7$)-cycloalkyl, ($C_3$–$C_7$)-cycloalkyl-($C_1$–$C_4$)-alkylene, COOH, COO—($C_1$–$C_6$)-alkyl, CO—$NH_2$, CO—NH—($C_1$–$C_6$)-alkyl, CO—N—[($C_1$–$C_6$)-alkyl]$_2$, CO—NH—($C_3$–$C_7$)-cycloalkyl, $NH_2$, NH—($C_1$–$C_6$)-alkyl, N—[($C_1$–$C_6$)-alkyl]$_2$, NH—CO—($C_1$–$C_6$)-alkyl, NH—CO-phenyl, or NH—$SO_2$-phenyl, wherein the phenyl of NH—CO-phenyl and NH—$SO_2$-phenyl is unsubstituted or substituted 1 or 2 times wherein each substituent is independently chosen from F, Cl, CN, OH, ($C_1$–$C_6$)-alkyl, O—($C_1$–$C_6$)-alkyl, $CF_3$, $OCF_3$, COOH, COO—($C_1$–$C_6$)-alkyl and CO—$NH_2$;

R7 is H, ($C_1$–$C_6$)-alkyl, or CO($C_1$–$C_6$)-alkyl;

R8 is H, ($C_1$–$C_{10}$)-alkyl, where the alkyl is unsubstituted or substituted 1, 2, or 3 times wherein each substituent is independently chosen from OH, $CF_3$, CN, COOH, COO—($C_1$–$C_6$)-alkyl, CO—$NH_2$, $NH_2$, NH—($C_1$–$C_6$)-alkyl, N—[($C_1$–$C_6$)-alkyl]$_2$, NCO—($C_1$–$C_6$)-alkyl, NCOO—($C_1$–$C_6$)-alkyl, NCOO—($C_1$–$C_6$)-alkenyl, NCOO—($C_1$–$C_6$)-alkynyl and NCOO—($C_1$–$C_4$)-alkylene-($C_6$–$C_{10}$)-aryl; or $(CH_2)_m$-aryl, where m ranges from 0–6, and aryl is phenyl, O-phenyl, CO-phenyl, tetrahydronaphthyl or naphthyl, where the aryl is unsubstituted or substituted by at least one R9;

R9 is F, Cl, Br; OH, $NO_2$, $CF_3$, $OCF_3$, ($C_1$–$C_6$)-alkyl, ($C_1$–$C_6$)-alkyl-OH, O—$C_1$–$C_6$)-alkyl, S—($C_1$–$C_6$)-alkyl, ($C_1$–$C_4$)-alkylphenyl, COOH, or COO—($C_1$–$C_6$)-alkyl;

and physiologically tolerable salts thereof, in any stereoisomeric form.

\* \* \* \* \*